(12) United States Patent
Broen et al.

(10) Patent No.: US 9,907,892 B2
(45) Date of Patent: Mar. 6, 2018

(54) PORTABLE CONTROLLER AND POWER SOURCE FOR MECHANICAL CIRCULATION SUPPORT SYSTEMS

(75) Inventors: Kenneth E. Broen, Birchwood, MN (US); Corey D. Brown, Coon Rapids, MN (US); Don W. E. Evans, St. Paul, MN (US); David J. Hansen, Stillwater, MN (US); Anne F. Mickelson, Stillwater, MN (US); Richard A. Nazarian, Excelsior, MN (US)

(73) Assignee: Minnetronix Inc., St. Paul, MN (US)

( * ) Notice: Subject to any disclaimer, the term of this patent is extended or adjusted under 35 U.S.C. 154(b) by 1621 days.

(21) Appl. No.: 13/040,925

(22) Filed: Mar. 4, 2011

(65) Prior Publication Data

US 2011/0218383 A1 Sep. 8, 2011

Related U.S. Application Data

(60) Provisional application No. 61/311,078, filed on Mar. 5, 2010, provisional application No. 61/416,626, filed on Nov. 23, 2010.

(51) Int. Cl.
*A61M 1/12* (2006.01)

(52) U.S. Cl.
CPC ......... *A61M 1/127* (2013.01); *A61M 2205/17* (2013.01); *A61M 2205/3523* (2013.01); *A61M 2205/8212* (2013.01); *A61M 2205/8243* (2013.01)

(58) Field of Classification Search
USPC .......................................................... 600/16
See application file for complete search history.

(56) References Cited

U.S. PATENT DOCUMENTS

| | | | |
|---|---|---|---|
| 3,633,217 A | 1/1972 | Lance | |
| 4,957,504 A | 9/1990 | Chardack | |
| 4,991,340 A * | 2/1991 | Schildt | 43/81 |
| 5,088,037 A * | 2/1992 | Battaglia | 600/300 |
| 5,089,017 A | 2/1992 | Young et al. | |
| 5,569,156 A | 10/1996 | Mussivand | |
| 5,613,935 A | 3/1997 | Jarvik | |
| 5,645,586 A * | 7/1997 | Meltzer | 623/11.11 |
| 5,766,207 A | 6/1998 | Potter et al. | |

(Continued)

FOREIGN PATENT DOCUMENTS

| | | |
|---|---|---|
| EP | 0760244 A1 | 3/1997 |
| GB | 2140193 A | 11/1984 |

(Continued)

OTHER PUBLICATIONS

Office Action from U.S. Appl. No. 13/788,963, dated Dec. 13, 2013, 6 pp.

(Continued)

*Primary Examiner* — Amanda Patton
(74) *Attorney, Agent, or Firm* — Shumaker & Sieffert, P.A.

(57) ABSTRACT

A portable external device for a mechanical circulation support system includes first and second power sources, e.g. batteries and control electronics for redundant uninterrupted operation of an implantable blood pump. The control and power source module may be configured for variable form factors to accommodate a variety of wearable configurations for patient convenience and comfort.

50 Claims, 22 Drawing Sheets

(56) References Cited

U.S. PATENT DOCUMENTS

| | | | |
|---|---|---|---|
| 5,999,133 A * | 12/1999 | Svensson | H01Q 1/244 343/702 |
| 6,048,363 A | 4/2000 | Nagyszalanczy et al. | |
| 6,183,412 B1 * | 2/2001 | Benkowski et al. | 600/16 |
| 6,264,601 B1 | 7/2001 | Jassawalla et al. | |
| 6,658,275 B1 * | 12/2003 | Hantunen | H04M 1/215 379/433.13 |
| 6,977,479 B2 * | 12/2005 | Hsu | 320/101 |
| 7,105,022 B2 | 9/2006 | Yoon et al. | |
| 7,561,686 B2 * | 7/2009 | Vance | 379/433.13 |
| 7,585,322 B2 | 9/2009 | Azzolina | |
| 7,684,864 B2 * | 3/2010 | Olson et al. | 607/36 |
| 7,946,984 B2 * | 5/2011 | Brister et al. | 600/365 |
| 8,394,009 B2 | 3/2013 | Bolyard et al. | |
| 2001/0037093 A1 | 11/2001 | Benkowski et al. | |
| 2002/0052539 A1 * | 5/2002 | Haller et al. | 600/300 |
| 2003/0069465 A1 | 4/2003 | Benkowski et al. | |
| 2003/0114899 A1 * | 6/2003 | Woods | A61N 1/36071 607/60 |
| 2004/0059205 A1 * | 3/2004 | Carlson et al. | 600/310 |
| 2005/0071001 A1 * | 3/2005 | Jarvik | A61M 1/122 623/3.28 |
| 2005/0101875 A1 * | 5/2005 | Semler et al. | 600/509 |
| 2005/0151502 A1 | 7/2005 | Quirion | |
| 2006/0058873 A1 | 3/2006 | Peralta | |
| 2007/0142696 A1 | 6/2007 | Crosby et al. | |
| 2007/0197854 A1 | 8/2007 | Marsielle et al. | |
| 2008/0294252 A1 | 11/2008 | Myklebust | |
| 2008/0306329 A1 | 12/2008 | Lu et al. | |
| 2009/0118592 A1 * | 5/2009 | Klitgaard | A61B 5/6849 600/300 |
| 2009/0118827 A1 * | 5/2009 | Sugiura | 623/3.1 |
| 2009/0149951 A1 | 6/2009 | Sugiura et al. | |
| 2009/0154883 A1 * | 6/2009 | Robb | H01R 35/04 385/56 |
| 2010/0151699 A1 * | 6/2010 | Cho | H01R 35/04 439/13 |
| 2011/0184289 A1 | 7/2011 | Oshiki et al. | |

FOREIGN PATENT DOCUMENTS

| | | |
|---|---|---|
| JP | 2004111242 A | 4/2004 |
| JP | 2005216631 A | 8/2005 |
| JP | 2007335132 A | 12/2007 |
| JP | 2008544441 A | 12/2008 |
| JP | 2009524504 A | 7/2009 |
| WO | 9908745 A1 | 2/1999 |
| WO | 9917819 A1 | 4/1999 |
| WO | 2007053881 A1 | 5/2007 |
| WO | 2007070932 A1 | 6/2007 |
| WO | 2007072025 A2 | 6/2007 |
| WO | 2008154387 A1 | 12/2008 |

OTHER PUBLICATIONS

Office Action from U.S. Appl. No. 13/041,221, dated Jul. 27, 2012, 6 pp.

Response to Office Action dated May 10, 2013, from U.S. Appl. No. 13/041,220, filed Jul. 10, 2013, 12 pp.

Tursini et al., "Speed and position estimation for PM synchronous motor with back-EMF observer," conference Record of the 2005 IEEE Industry Applications Conference Fortieth IAS Annual Meeting, IEEE cat. No. 05, vol. 3., Oct. 2, 2005, pp. 2083-2090.

International Search Report and Written Opinion of corresponding international application No. PCT/US2011/027258, dated Aug. 2, 2011, 9 pp.

Office Action from U.S. Appl. No. 13/041,220, dated Oct. 5, 2012, 10 pp.

Response to Office Action dated Jul. 27, 2012, from U.S. Appl. No. 13/041,221, filed Oct. 26, 2012, 15 pp.

Response to an Office Action from the counterpart Canadian patent application No. 2,791,902, filed Apr. 2, 2014, 11 pp.

Response to first Examination Report from counterpart Australian patent application No. 2011222567, dated Dec. 18, 2013, 16 pp.

Food and Drug Administration, Approval documentation for "Thoratec HeartMate II® Left Ventricular Assist System (LVAS)", Thoratec Corporation, Apr. 21, 2008,3 pages, http://www.accessdata.fda.gov/cdrh_docs/pdf6/P060040A.pdf.

"HeartMate II® Left Ventricular Assist System", Thoratec Corporation, 2 pages, accessed from the internet on Aug. 9, 2011 at url http://www.thoratec.com/medical-professionals/vad-product-informaton/heartmate-II-lvad.aspx.

Response to Office Action dated Oct. 5, 2012, from U.S. Appl. No. 13/041,220, filed Jan. 4, 2013, 16 pp.

Notice of Allowance from U.S. Appl. No. 13/041,221, dated Nov. 5, 2012, 5 pp.

Final Office Action from U.S. Appl. No. 13/041,220, dated May 10, 2013, 5 pp.

Office Action from Counterpart Canadian patent application No. 2,791,902, dated Oct. 11, 2013, 2 pages.

The Notification of Transmittal of the International Preliminary Report on Patentability dated Apr. 16, 2012 for counterpart application No. PCT/US2011/027258, 18 pages.

Reply to Written Opinion dated Aug. 2, 2011, for corresponding international application No. PCT/US2011/027258, filed Jan. 5, 2012, 17 pp.

Examiner's Report from corresponding Australian Patent Application No. 2011222567, dated Mar. 5, 2013, 2 pp.

Notice of Reasons for Rejection, and translation thereof, from Counterpart Japanese Patent Application No. 2012-556268, dated Dec. 2, 2014, 5 pp.

* cited by examiner

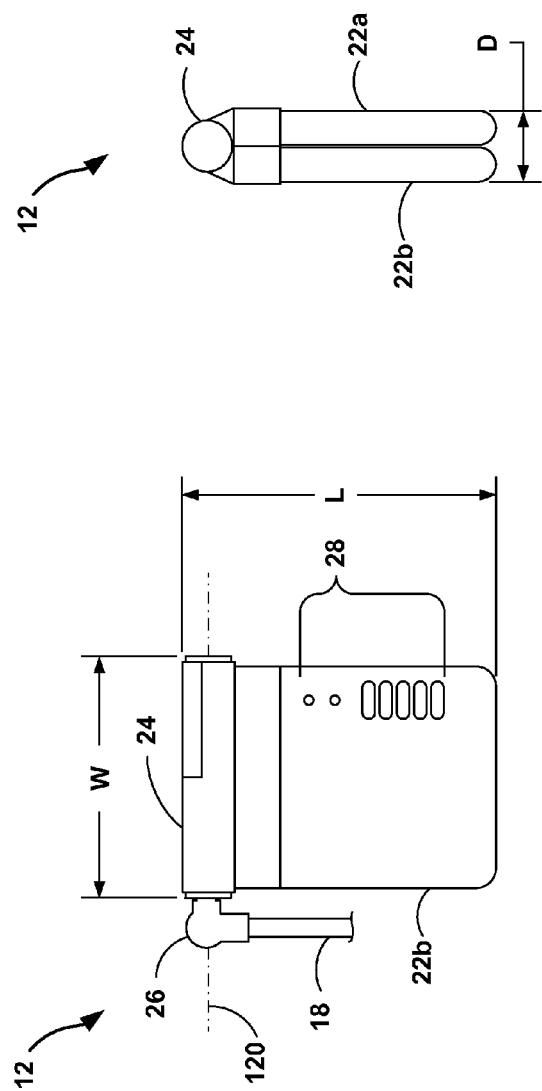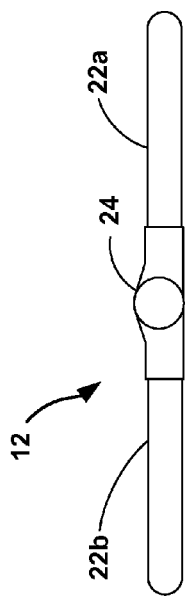

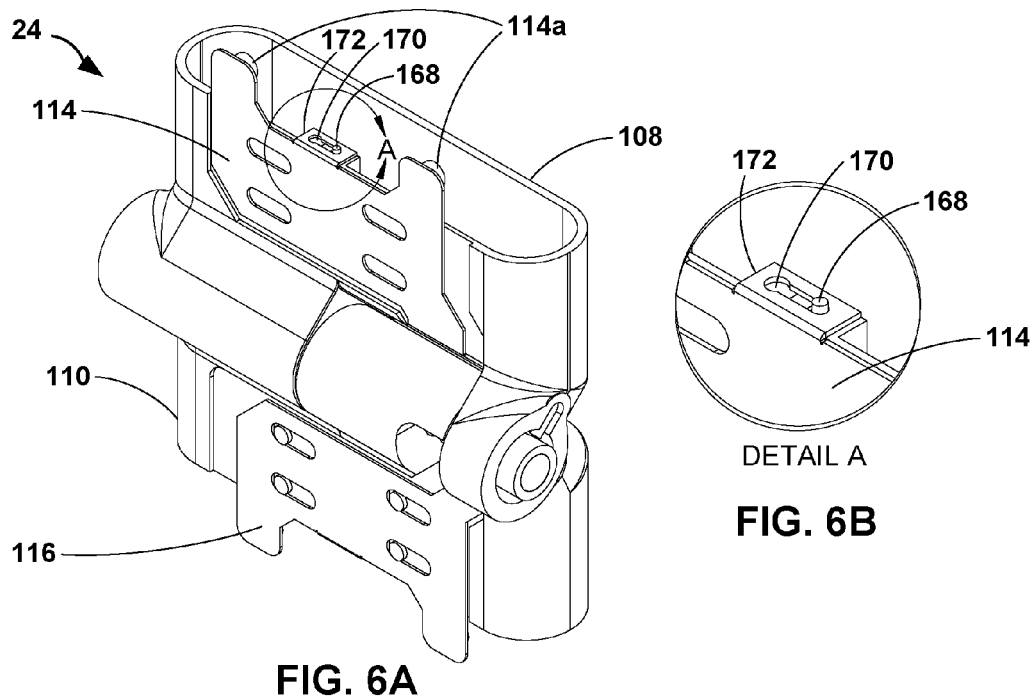
FIG. 6A
DETAIL A
FIG. 6B
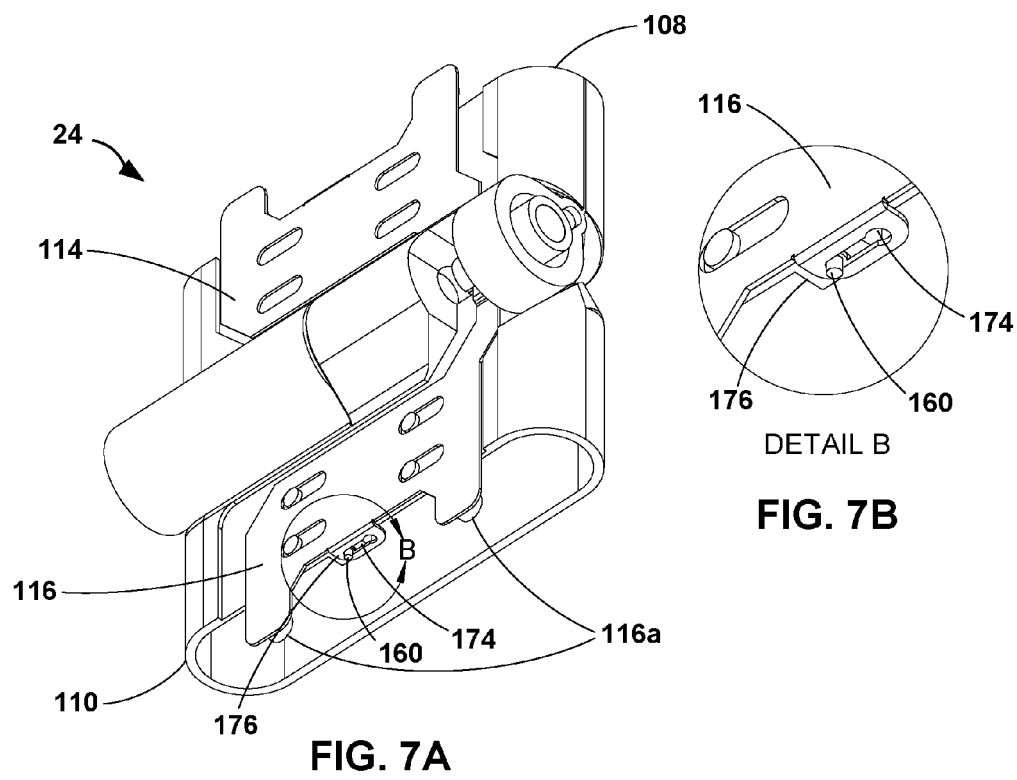
FIG. 7A
DETAIL B
FIG. 7B

DETAIL C

SECTION D-D

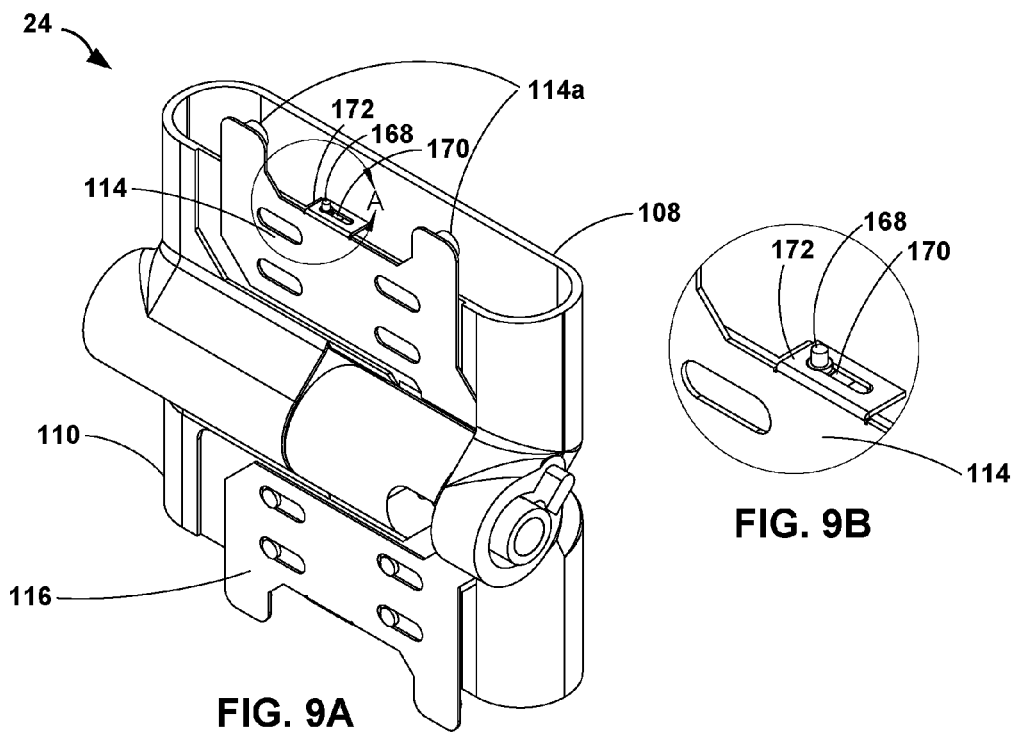
FIG. 9A
FIG. 9B
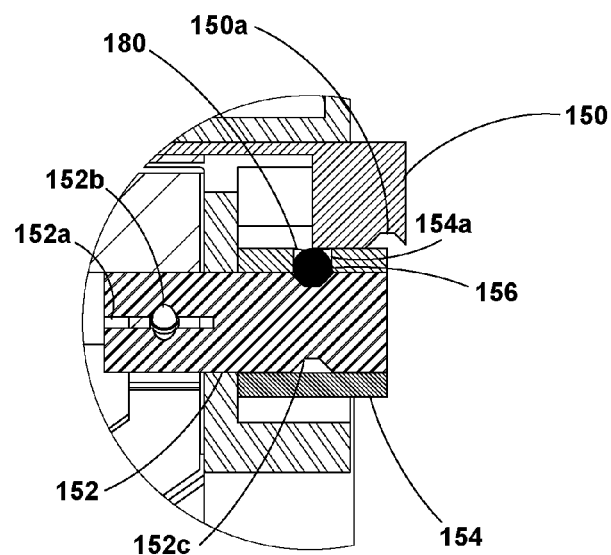
FIG. 9C

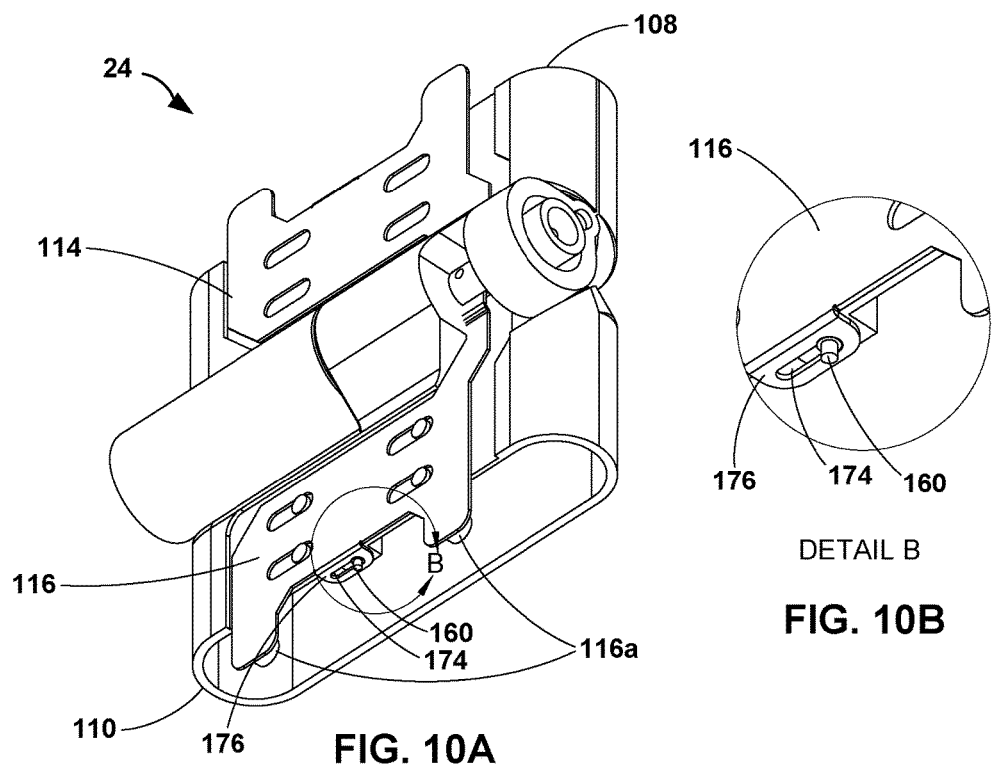
FIG. 10A
DETAIL B
FIG. 10B
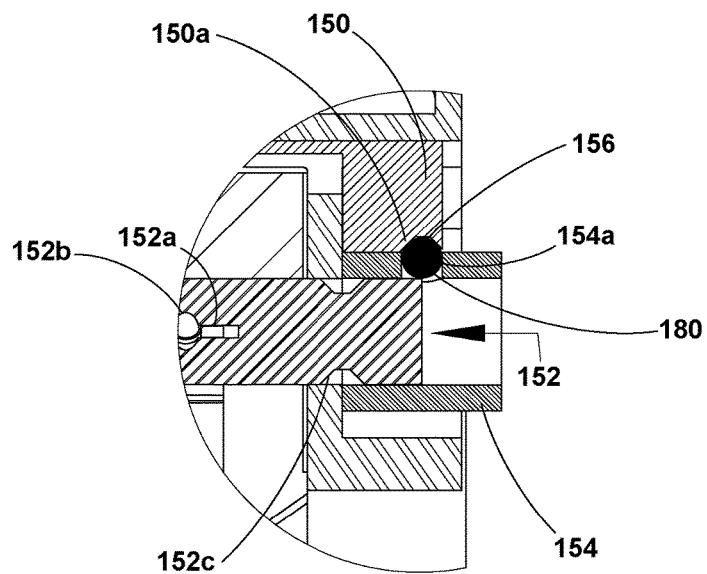
FIG. 10C

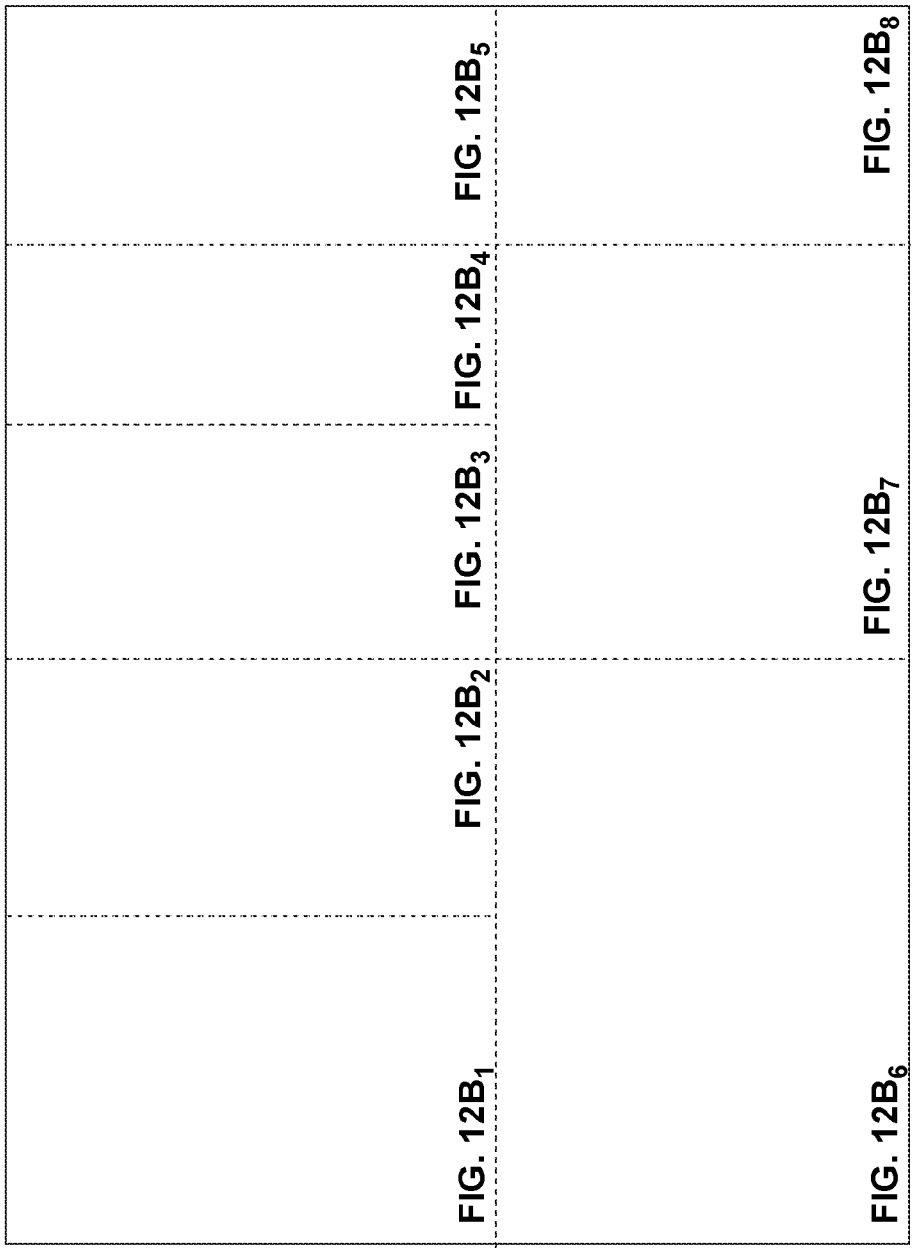

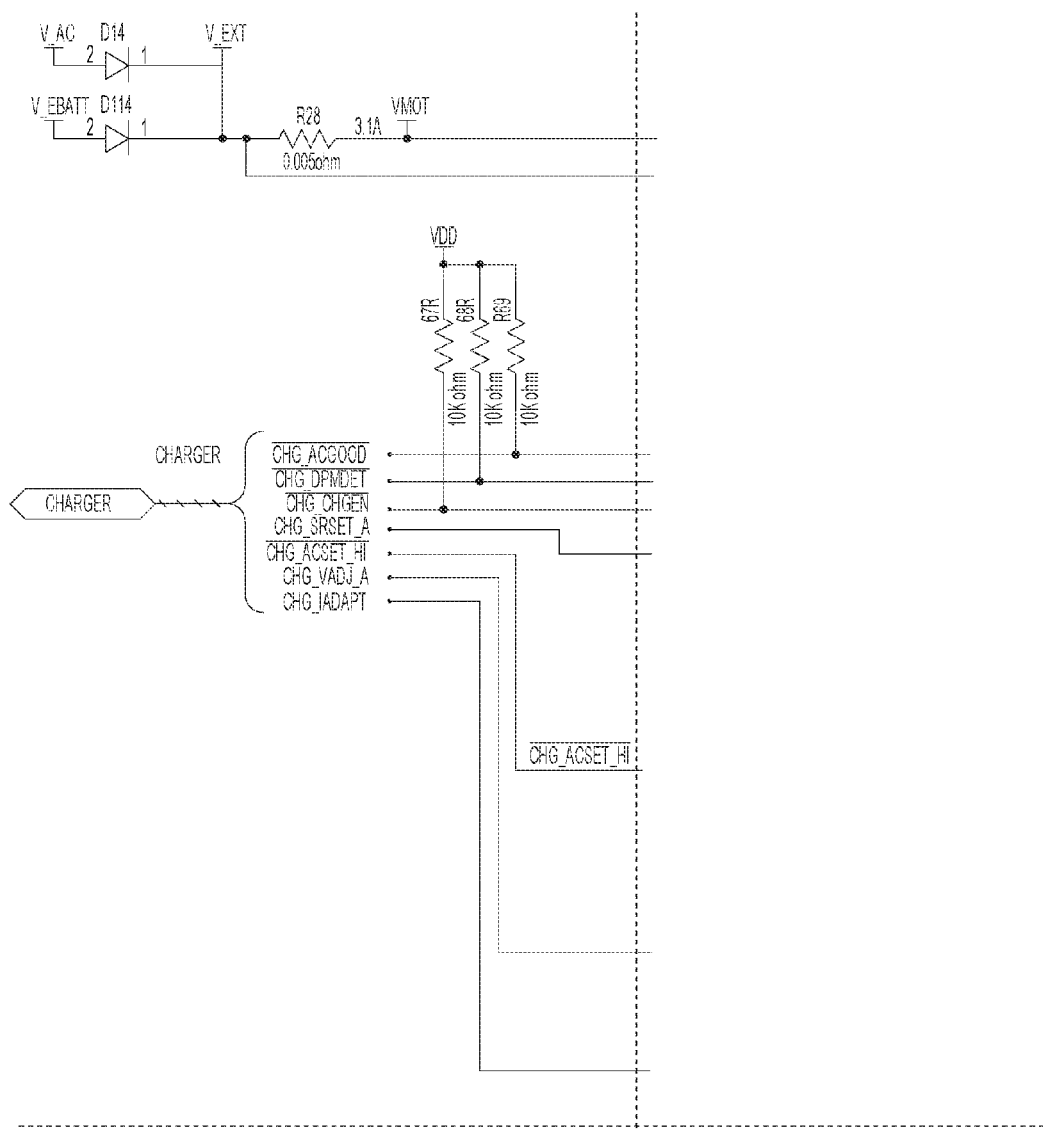
FIG. 12B₁

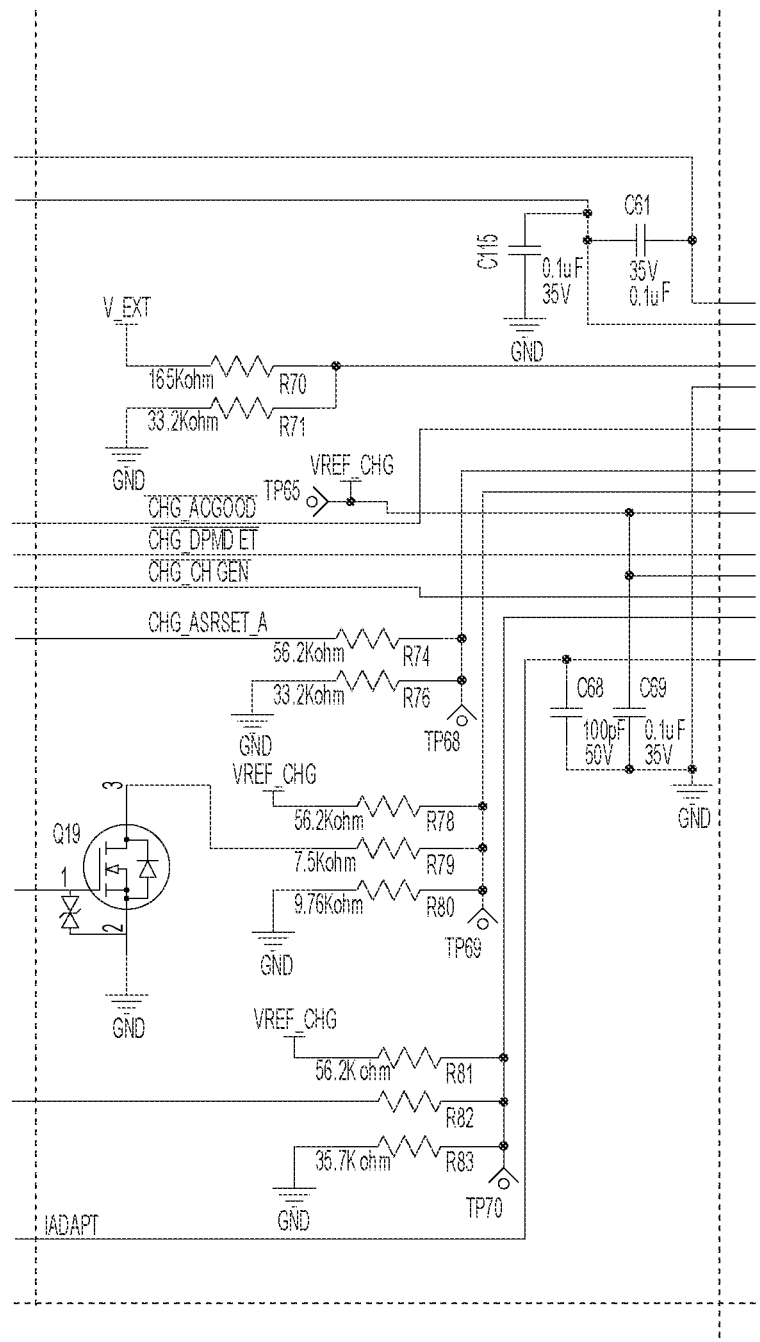
FIG. 12B₂

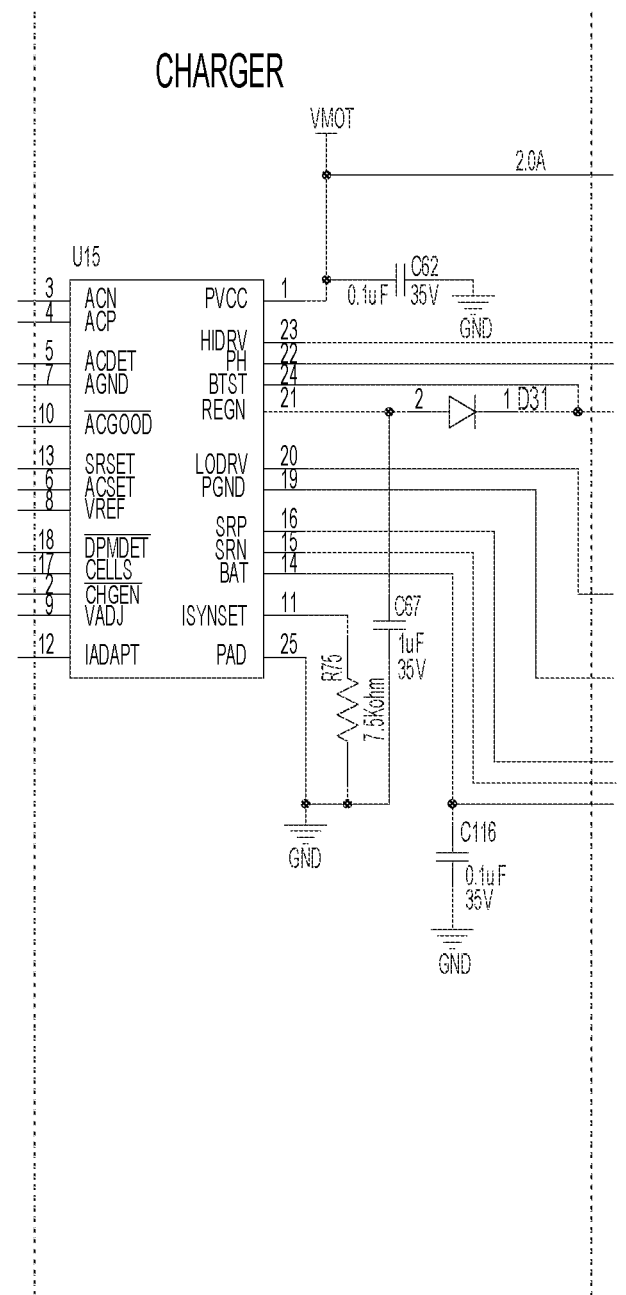
FIG. 12B$_3$

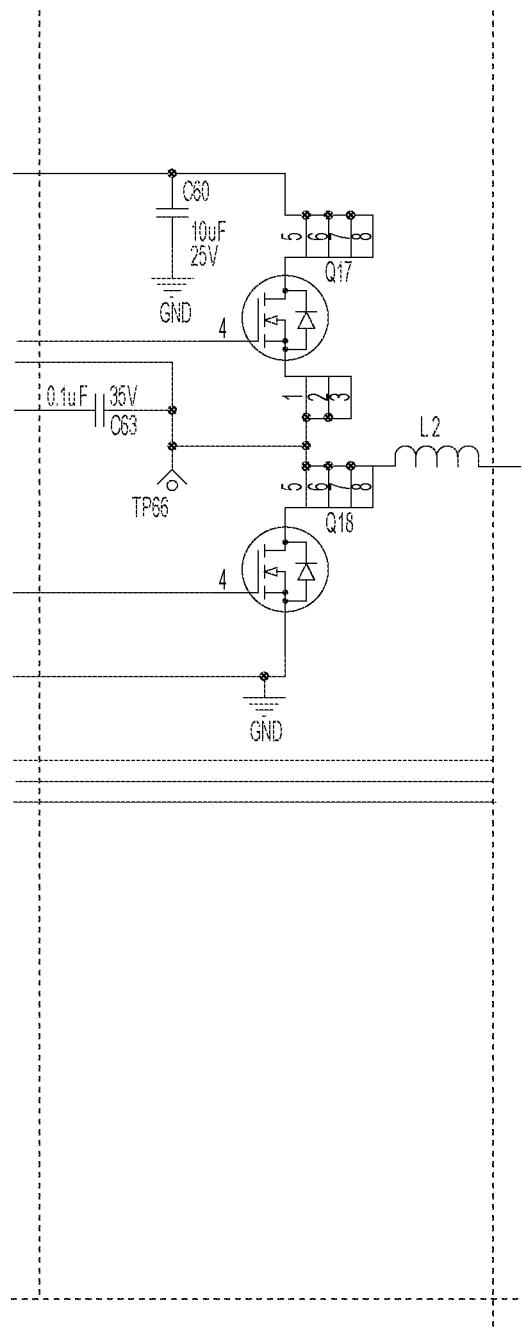
FIG. 12B₄

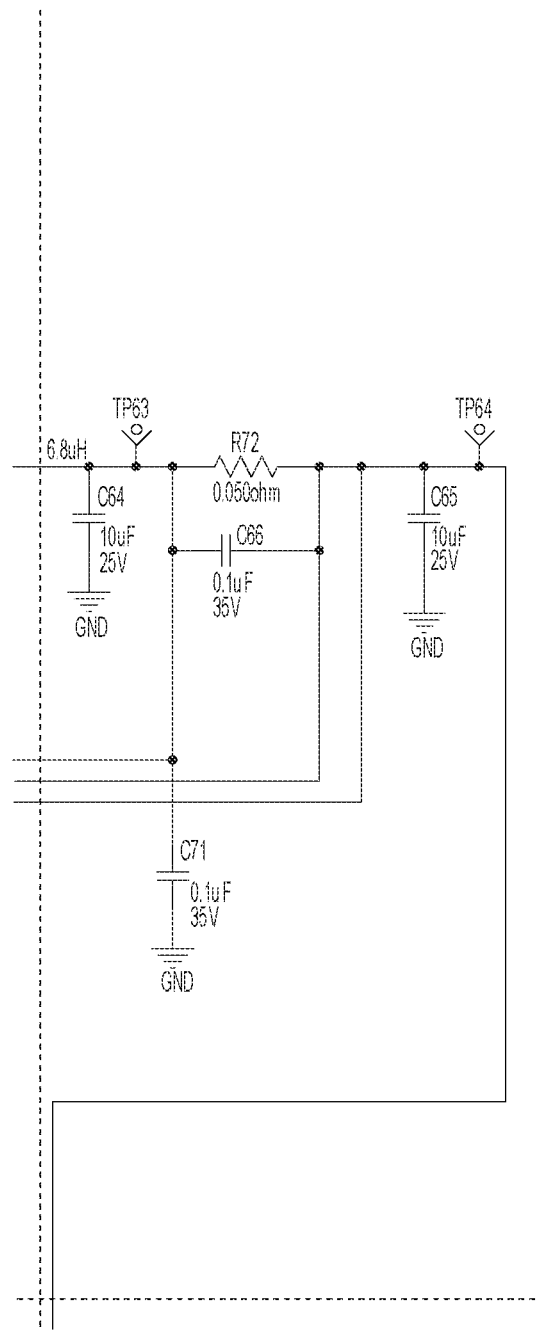
FIG. 12B₅

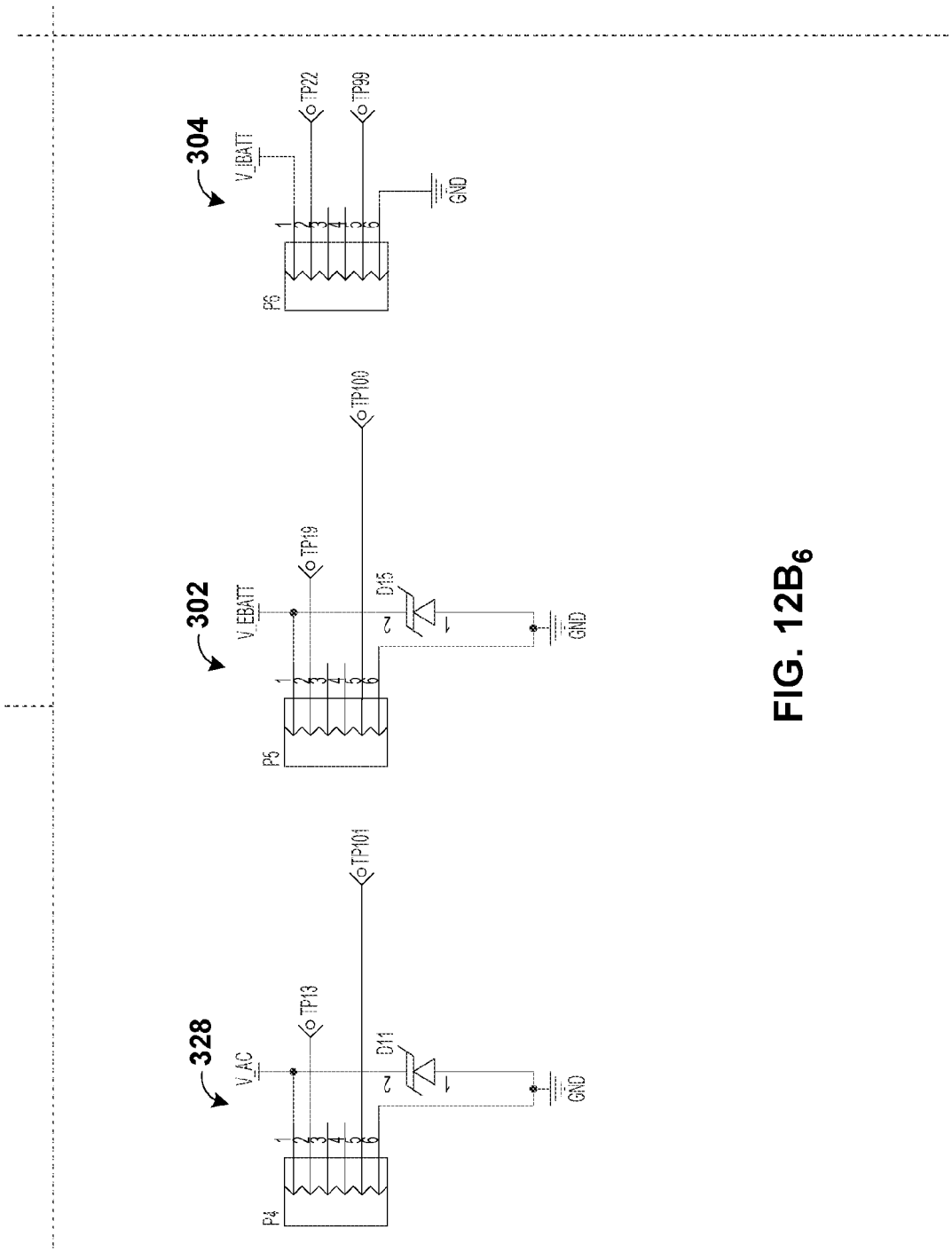
FIG. 12B₆

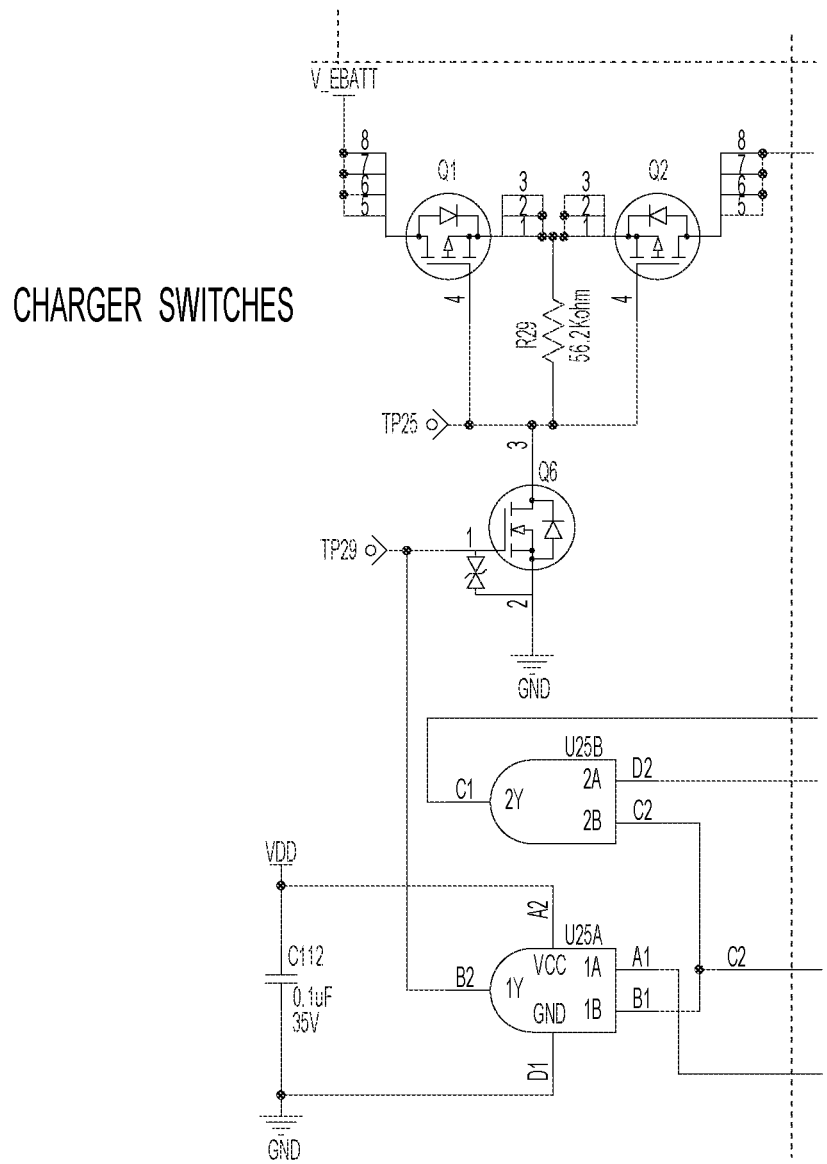
FIG. 12B$_7$

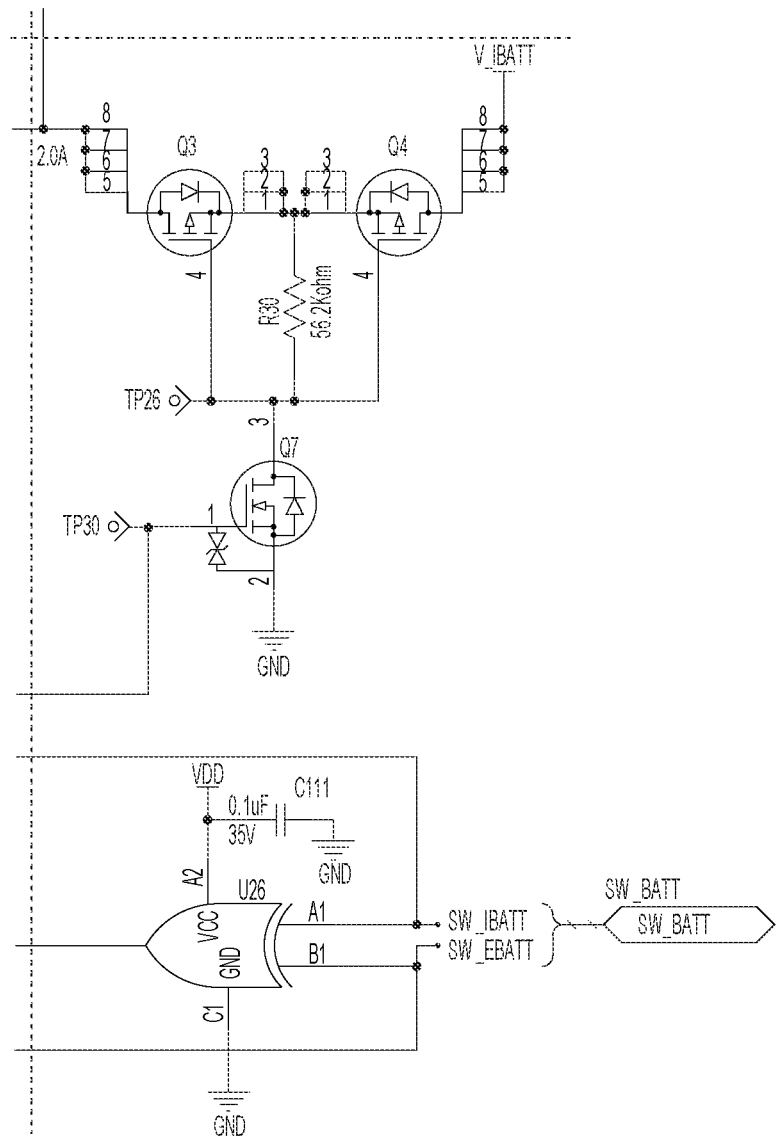
FIG. 12B₈

PORTABLE CONTROLLER AND POWER SOURCE FOR MECHANICAL CIRCULATION SUPPORT SYSTEMS

This application claims the benefit of U.S. Provisional Application No. 61/311,078, filed Mar. 5, 2010, and U.S. Provisional Application No. 61/416,626, filed Nov. 23, 2010, both of which are incorporated herein in their entireties by this reference.

BACKGROUND

Generally speaking, heart failure is a major public health problem affecting a great number of people. Heart transplantation has been one of the most effective therapies for treating heart failure. However, transplantations may be limited by complications from long-term immunosuppressive therapy, allograft coronary artery diseases, as well as the limited number of donor organs.

Mechanical circulation support (MCS) systems, both total artificial hearts (TAH) and ventricular assist devices (VAD) have been studied in the hopes of augmenting or replacing the role of heart transplantation for heart failure patients. A VAD may be a left ventricular assist device (LVAD), a right ventricular assist device (RVAD) or a biventricular assist device (bi-VAD). Generally speaking, VADs may be employed to provide heart failure patients with therapies including as a bridge to or recovery from heart transplantation, as well as a long-term alternative to the transplantation.

TAHs and VADs are blood pumping devices connected to a patient to receive blood from a source and pump the blood to one or more destinations within the body of the patient. For example, an LVAD receives blood from the atrium or ventricle of a patient and pumps the blood into the aorta. An RVAD, on the other hand, receives blood from the atrium or ventricle and pumps the blood it into the pulmonary artery. An MCS generally includes external components including, e.g., control electronics and power sources connected by one or more percutaneous cables to internal components including, e.g., a blood pump. As a patient resumes regular activities after receiving an MCS, the design and configuration of the MCS equipment they wear becomes an important aspect of their safety and comfort.

SUMMARY

In general, the techniques described herein are directed to a portable external device for a mechanical circulation support system that includes first and second power sources, e.g. batteries and control electronics for redundant uninterrupted operation of an implantable blood pump.

In one example, a portable external device for a mechanical circulation support system includes a first power source, a second power source, a hinged housing, and control electronics. The hinged housing is interposed between and configured to receive the first and second power sources. The control electronics are arranged within the hinged housing.

In another example, a mechanical circulation support system includes an implantable pump and a portable external device. The portable external device includes a first power source, a second power source, a hinged housing, and control electronics. The hinged housing is interposed between and configured to receive the first and second power sources. The control electronics are arranged within the hinged housing. At least one of the first power source and the second power source is configured to power the implantable pump.

The details of one or more examples are set forth in the accompanying drawings and the description below. Other features, objects, and advantages of such examples will be apparent from the description and drawings, and from the claims.

BRIEF DESCRIPTION OF DRAWINGS

FIGS. 4A-4C are conceptual diagrams illustrating an example control and power source module in multiple positions.

FIGS. 6A and 6B are perspective and detail views, respectively, of a first battery lock plate of an example battery locking mechanism in a locked position.

FIGS. 7A and 7B are perspective and detail views, respectively, of a second battery lock plate of an example battery locking mechanism in a locked position.

FIGS. 9A, 9B, and 9C are perspective, detail, and section views, respectively, illustrating actuation of the first battery lock plate.

FIGS. 10A, 10B, and 10C are perspective, detail, and section views, respectively, illustrating actuation of the second battery lock plate.

Figure 12A:
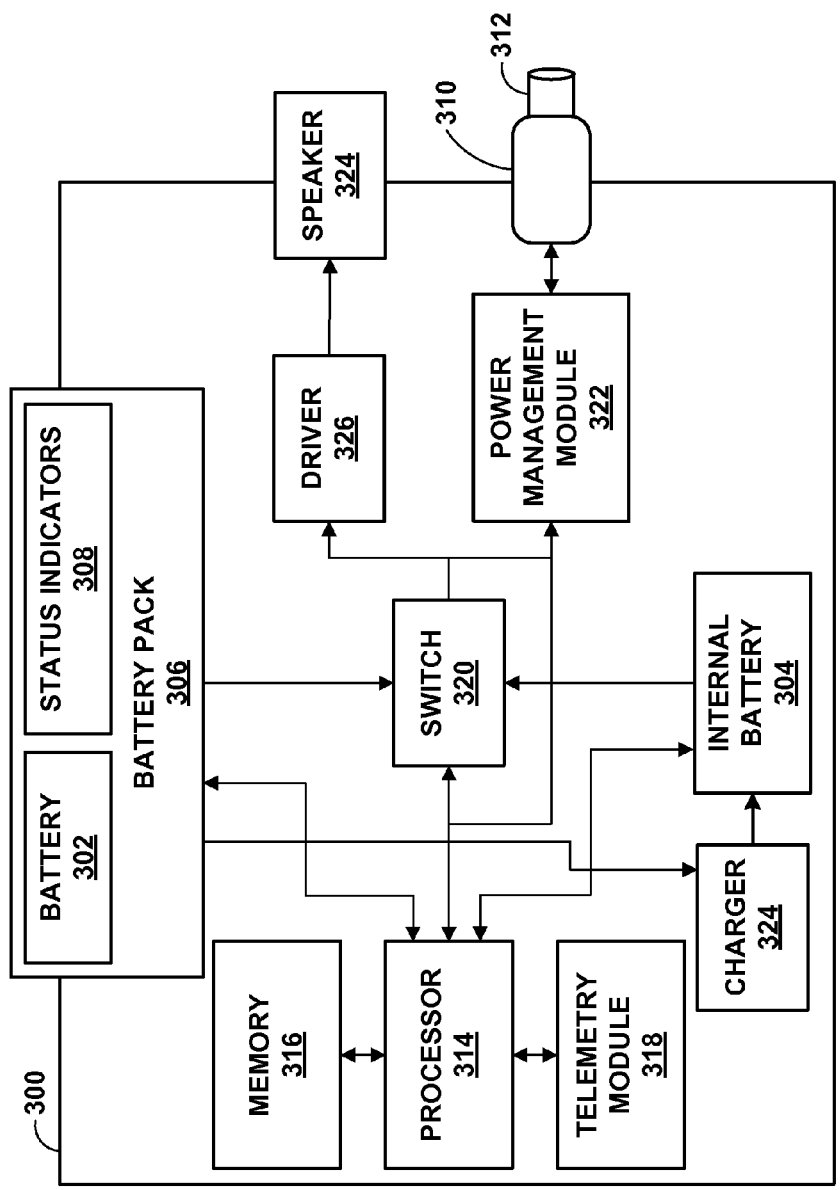
FIG. 12A is a functional block diagram illustrating components of an example external control and power source module including a removable external battery and internal non-removable back-up battery.

FIGS. $12B_1$-$12B_8$ ("FIG. 12") is illustrate an example charger circuit that may be employed in the external control and power source module of FIG. 12A.

Figure 12C:
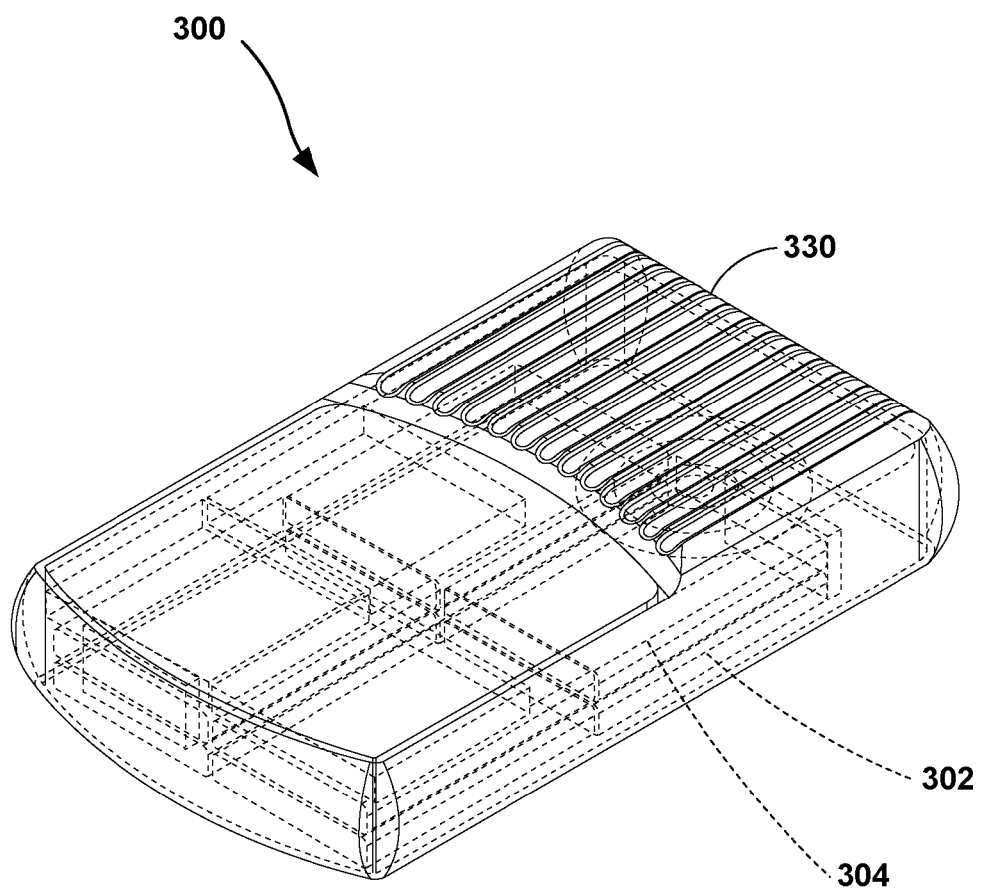

FIG. 12C is an example of the external control and power source module of FIG. 12A including a non-hinged housing.

Figure 13:
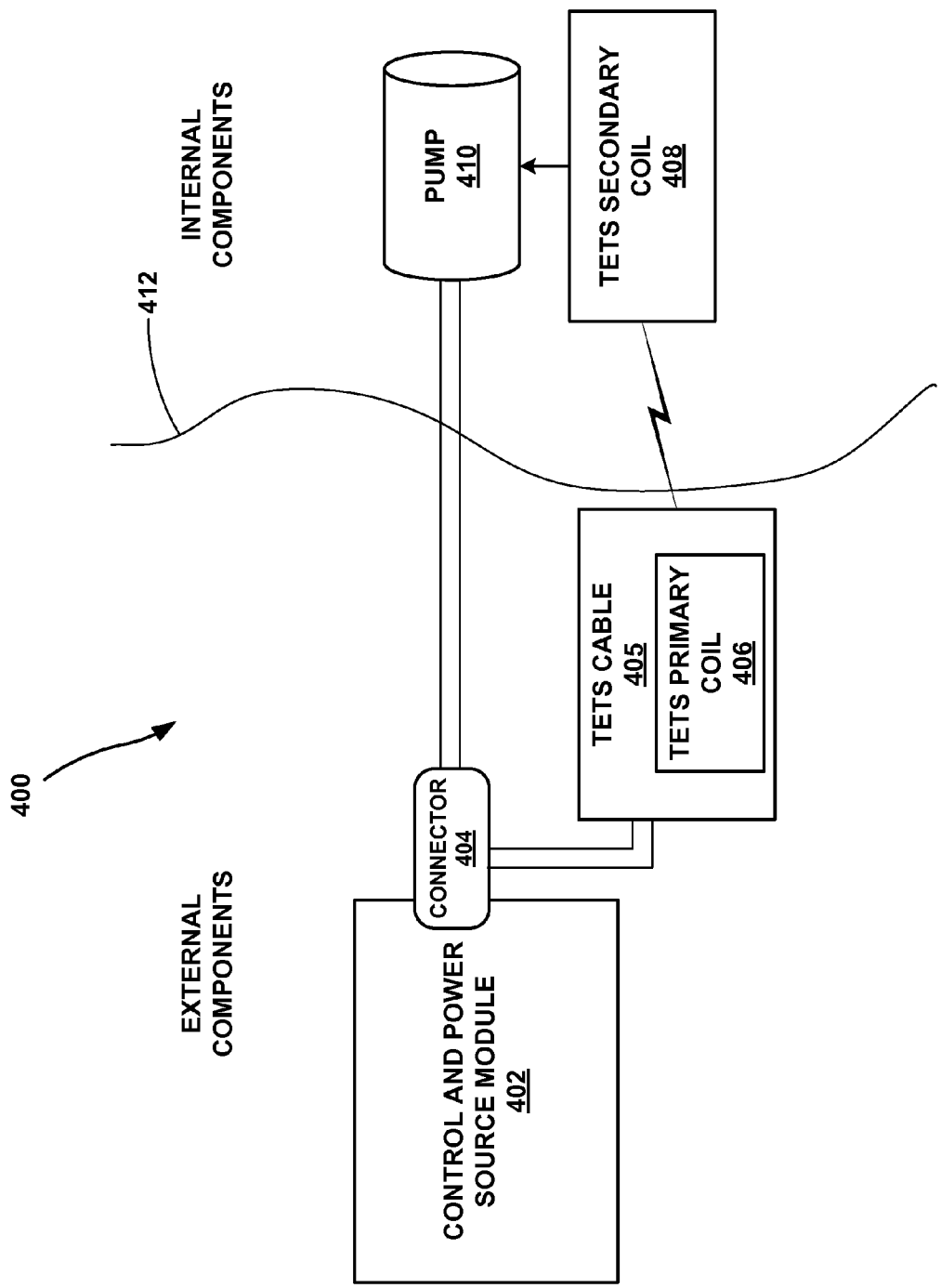

FIG. 13 is a schematic illustration of a ventricular assist device (VAD) including a control and power source module that functions as a transcutaneous energy transfer system (TETS).

DETAILED DESCRIPTION

Figure 1:
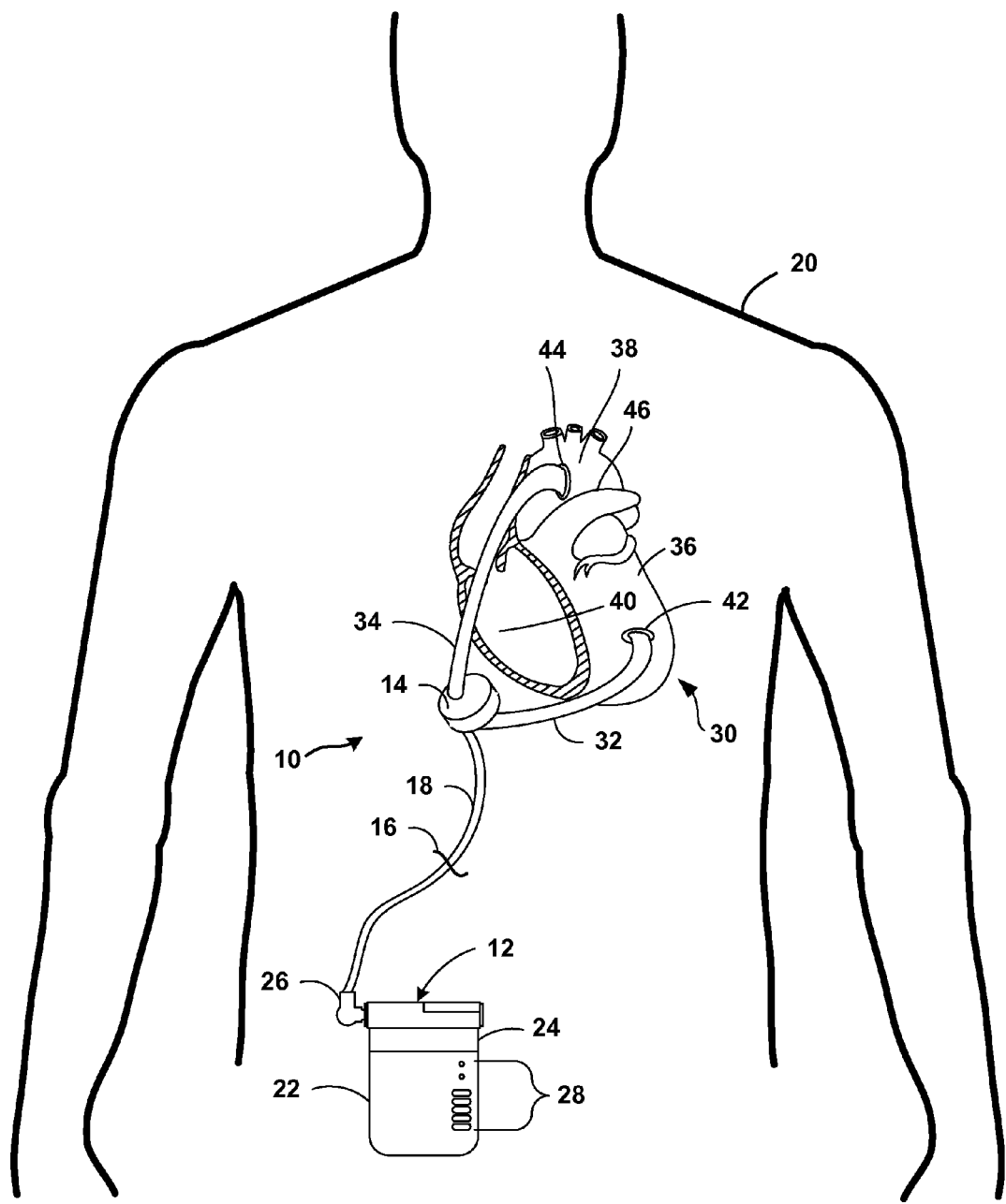
FIG. 1 is a conceptual diagram illustrating an example left ventricular assist device (LVAD) including a portable external control and power source module.

FIG. 1 is a conceptual diagram illustrating an example left ventricular assist device (LVAD) 10 including portable control and power source module 12 percutaneously connected to implanted pump 14 through incision 16 by cable 18. Control and power source module 12 is a portable external device configured for variable form factors to accommodate a variety of wearable configurations for patient 20. Control and power source module 12 generally includes two battery packs 22, only one of which is viewable in FIG. 1, hinged housing 24, connector 26, and status indicators 28. Battery packs 22 each include a battery connected to hinged housing 24 to form a clam shell assembly configured to fold the two batteries in a generally parallel stacked relationship with one another, as illustrated in FIG. 1, and to rotate the two batteries from the stacked relationship into generally coplanar relationship with one another with each of the first and second batteries extending in opposing directions from the hinged housing (see FIGS. 3 and 4A-4C). Cable 18 interfaces control and power source module 12 via connector 26 to communicate power and other signals between the external module and implanted pump 14. As will be discussed in greater detail with reference to FIG. 2, control and power source module 12 also includes control electronics (not shown in FIG. 1) configured to control operation of various components of LVAD 10 including pump 14, the batteries of battery packs 22, and status indicators 28. Status indicators 28, generally speaking, are visual indicators incorporated into each of the two battery packs 22 to provide information to patient 20 including, e.g., a gauge of the remaining charge left in each of the batteries of the battery packs.

Pump 14 of LVAD 10 may be surgically implanted within patient 20 including, e.g., in the abdominal cavity of the patient as illustrated in the example of FIG. 1. In other examples, pump 14 may be implanted in other locations within patient 20. Pump 14 is connected to heart 30 of patient 20 by inlet and outlet cannula 32, 34. In the example LVAD 10 of FIG. 1, inlet cannula 32 communicates blood from left ventricle 36 (LV) of heart 30 pump 14. Outlet cannula 34 communicates blood from pump 14 to aorta 38 of patient 20. Pump 14 includes a rigid housing formed from or with a biocompatible material or coating that resists corrosion and degradation from bodily fluids. Examples of suitable biocompatible materials include titanium and biologically inert polymers. Pump 14 may include a variety of types of positive displacement mechanisms capable of drawing blood into and ejecting the blood out of the pump. For example, pump 14 may include one of a centrifugal impeller, peristaltic, electromagnetic piston, axial flow turbine pump, magnetic bearing rotary pump, pneumatic displacement pump or another positive displacement mechanism appropriate for use with implantable devices such as RVAD 10.

In the example of FIG. 1, ventricular assist system 10 is illustrated assisting left ventricle 36 (LV) of heart 30 of patient 20. However, in other examples, the techniques disclosed may be employed in other types of mechanical circulation support (MCS) systems configurable to, e.g., assist right ventricle 40 in a right ventricular assist device (RVAD), as well as both ventricles 36, 40 in a biventricular assist device (BiVAD). As a general matter, therefore, the source of blood for example VADs may be described generally as the assisted ventricle, while the destination of the pressurized blood delivered by the VAD may be designated as the arterial vessel.

Referring again to FIG. 1, each of inlet and outlet cannulas 32, 34 may be formed from flexible tubine extending to left ventricle 36 and aorta 38, respectively. Inlet and outlet cannulas 32, 34 may be attached to tissue of left ventricle 36 and aorta 38, respectively, by, e.g., sutures to establish and maintain blood flow, and may include appropriate structure for such attachment techniques including, e.g. suture rings 42, 44. In any of the aforementioned LVAD, RVAD, or BiVAD configurations, inlet cannula 32 is anastomosed to the assisted ventricle (or ventricles), while outlet cannula 34 is anastomosed to the corresponding assisted arterial vessel, which for left ventricular assist is typically aorta 38 and for right ventricular assist is typically pulmonary artery 46.

Figure 2:
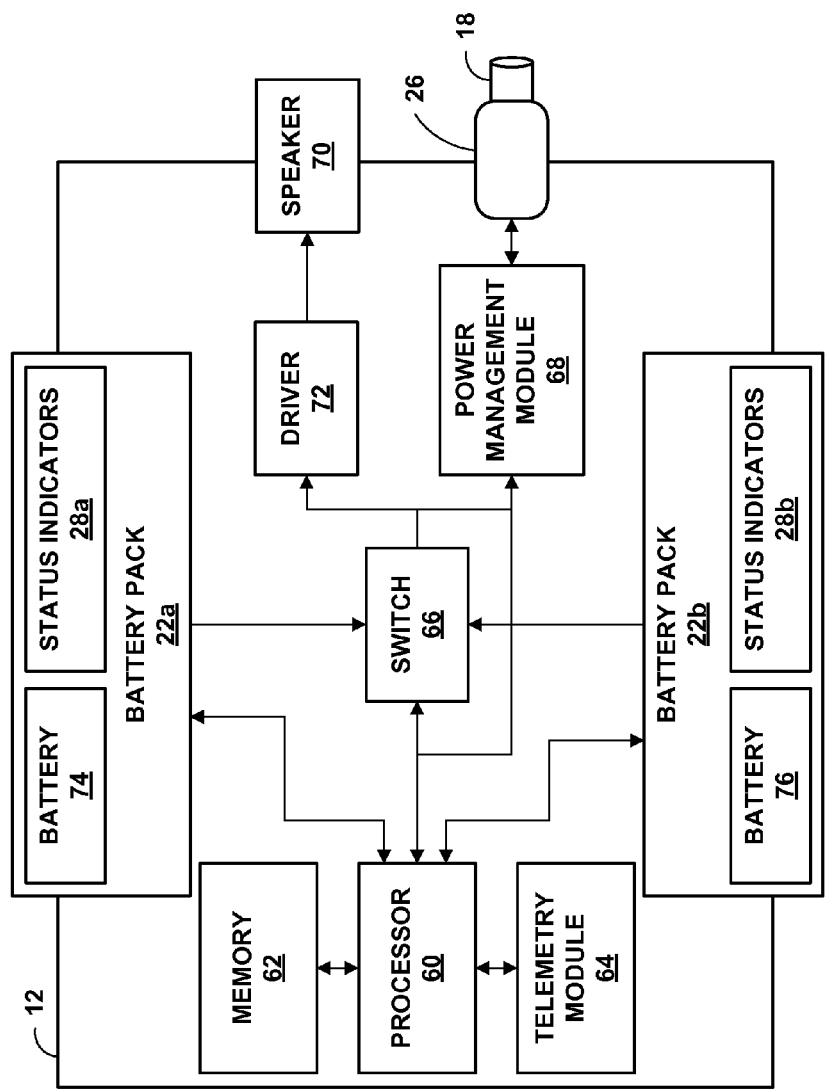
FIG. 2 is functional block diagram illustrating an example of the control and power source module of FIG. 1.

FIG. 2 is a functional block diagram illustrating components of an example of control and power source module 12, which includes first and second battery packs 22a, 22b, connector 26, and a variety of control electronics. The electronics of control and power source module 12 include processor 60, memory 62, telemetry module 64, a multiplexer with switch 66, and power management module 68. In some examples, control and power source module 12 also includes speaker 70 driven by driver 72 for emitting audible messages to patient 20 or a caregiver, such as a clinician.

First battery pack 22a includes first battery 74 and status indicators 28a. Similarly, second battery pack 22b includes second battery 76 and status indicators 28b. Each of first and second batteries 74, 76 may include, e.g., rechargeable lithium-ion (Li-ion), lithium polymer (Lipoly), nickel-metal hydride (NiMH), or nickel-cadmium (NiCd) battery cells. First and second battery 74, 76 generally function as primary and back-up power sources for pump 14 such that power is delivered to the pump without interruption. Each of first and second batteries 74, 76 are therefore removably connected to control and power source module 12 to allow each battery to be recharged as necessary. However, in order to protect against interrupting power to pump 14, control and power source module 12 includes a battery locking mechanism that prevents first battery 74 and second battery 76 from being removed from the device simultaneously.

In some examples, one or both of first and second batteries 74, 76 may be replaced by an external power source, including, e.g., an alternating or direct current (AC or DC respectively) power supply. In such examples, control and power source module 12, and, in particular, one or both of first and second battery packs 22a, 22b may include an adapter to which the external power source may connect. Additionally, the battery locking mechanism in such examples control and power source module 12 may be configured to prevent any primary and back-up power sources of the device from being removed or unplugged simultaneously, including external power sources like AC or DC power supplies.

Referring again to FIG. 2, Status indicators 28a, 28b for respective battery packs 22a, 22b may include a number of visual indicators for alerting patient 20 and other users to conditions and operation of control and power source module 12 and pump 14. For example, in the example shown in FIG. 1, status indicators 28a, 28b each include pump status indicator including of two LEDs respectively indicating green for normal operation and red for some malfunction or abnormality in the operation of pump 14 (FIG. 1). Additionally, each of status indicators 28a, 28b include a battery charge gauge including a number of LEDs the illumination of which indicate the level of charge remaining in each of first and second batteries 74, 76, respectively.

Control of control and power source module 12 and pump 14 is generally managed by processor 60. Processor 60 is communicatively connected to memory 62, telemetry module 64, power management module 68, speaker driver 72, and first and second battery packs 22a, 22b. Processor 60 stores data on and retrieves data from memory 62 related to the operation of pump 14, as well as, e.g., speaker 70. In particular, processor 60 may, e.g., retrieve information stored on memory 62 related to parameters for controlling pump 14 to pump blood through heart 30 of patient 20. In some examples, pump 14 may include an electric motor that drives operation of the pump to draw blood from left ventricle 36 and deliver it to aorta 38. For example, pump 14 may include any number of types of three-phase direct current (DC) or alternating current (AC) motors that are controlled by processor 60 based on parameters including, e.g., motor speed (RPM) and power range (nominal, high, max power in Watts), retrieved from memory 62.

Processor 60 may also receive feedback from pump 14 or other devices including, e.g., first and second batteries 74, 76 and store data related to the operation of the devices on memory 62. In one example, processor 60 measures voltage levels going to the phases of the motor of pump 14 and the current that is returning on these phases. Processor 60 may use this voltage and current information from pump 14, as well as characteristics of the pump, e.g. winding resistance and inductance to estimate the speed and the torque of the pump. Processor 60 may then execute a control loop that sets the speed of pump 14, which then sets the pump torque. The torque setting defines how much current processor 60 delivers to pump 14. In another example, processor 60 monitors the level of charge in each of first and second batteries 74, 76 and controls status indicators 28a, 28b, respectively, to indicate to patient 20 how much charge remains in each battery.

In some examples, control and power source module 12 is configured as a generic controller capable of controlling multiple types of pumps that include multiple types of motors. Generally speaking, many motors employed in implantable pumps of VADs will be able to be driven using a 3-phase bridge incorporated into control and power source module 12. The electronics of control and power source module 12 may be designed to drive and provide sensorless speed or torque control of virtually any permanent magnet motor. Control and power source module 12 may employ many different algorithms to control the motor of pump 14. Such algorithms, however, require some information about the motor parameters to be effective, such as the number of poles, the coil resistance, the coil inductance, as well as torque and speed constants. VAD controllers are commonly configured by selecting a set of motor parameters that work for a particular type or manufacturer motor. However, in some examples of control and power source module 12 described in this disclosure, the module, and, in particular, processor 60 may be configured to control a number of different types of motors by selecting a set of parameters that provide acceptable performance for all of the motors, instead of optimizing the parameters for a single motor.

In another example, processor 60 of control and power source module 12 discovers the kind of motor that drives pump 14 to provide a plug-and-play type interface that allows control and power source module 12 to adapt control parameters of pump 14 to the particular type of motor driving the pump. In some examples, each motor type may be assigned a unique identifier and processor 60 may query pump 14 to for this identifier. Processor 60 then retrieves a set of motor parameters associated with identifier from memory 62. In another example, processor 60 may execute an adaptive algorithm stored in memory 62 that determines the operational parameters of the motor driving pump 14 once control and power source module 12 is connected to the specific motor by cable 18. Such an adaptive algorithm may use the motor driver and sense circuitry to directly or indirectly measure the needed motor parameters.

Memory 62 of control and power source module 12 is a computer-readable storage medium that may be used to store data including instructions for execution by processor 60 or a processor of another device, such as, but not limited to, data related to the operation of pump 14 to assist heart 30 of patient 20. In some examples, memory 62 may store pump programs specific to, e.g., a particular pump motor that is controlled by processor 60 to drive pump 14. Memory 62 may include separate memories for storing instructions, patient information, pump or pump motor parameters (e.g., motor speed and power range), patient and pump operation histories, and other categories of information such as any other data that may benefit from separate physical memory modules. In some examples, memory 62 stores data that, when executed by processor 60, cause control and power source module 12 and pump 14 to perform the functions attributed to them in this disclosure.

Components described as processors within control and power source module 12, e.g. processor 60, or any other device described in this disclosure may each include one or more processors, such as one or more microprocessors, digital signal processors (DSPs), application specific integrated circuits (ASICs), field programmable gate arrays (FPGAs), programmable logic circuitry, or the like, either alone or in any suitable combination. Additionally, memory 62 and other computer readable storage media described in this disclosure may include a variety of types of volatile and non-volatile memory including, e.g., random access memory (RAM), static random access memory (SRAM), read only memory (ROM), programmable read only memory (PROM), erasable programmable read only memory (EPROM), electronically erasable programmable read only memory (EEPROM), flash memory, a hard disk, magnetic media, optical media, or other computer readable media.

In addition to processor 60 and memory 62, control and power source module 12 includes telemetry module 64. Generally speaking, telemetry module 64 facilitates wireless communications from and to control and power source module 12 and other devices including, e.g. a separate display device for presenting a user interface to patient 20 or another user like a clinician. Processor 60 therefore controls telemetry module 64 to wirelessly communicate between control and power source module 12 and other devices including, e.g. a separate user interface device. Telemetry module 64 in control and power source module 12, as well as telemetry modules in other devices described in this disclosure, can be configured to use RF communication techniques to wirelessly send and receive information to and from other devices respectively. Telemetry module 64 may, e.g., employ RF communication according to one of the 802.11, a Medical Implant Communication Service (MICS), Bluetooth or Bluetooth Low Energy specification sets, infrared (IR) communication according to the IRDA specification set, or another standard or proprietary telemetry protocol. Telemetry module 64 may send information from and receive information to control and power source module 12 on a continuous basis, at periodic intervals, or upon request from a user, e.g. patient 20 via a user interface device. In one example, telemetry module 64 communicates with a separate user interface device that includes a display, e.g. a liquid crystal display device (LCD) to display to patient 20 or another user the operation status of control and power source module 12 and pump 14, as well as the specific status of first and second batteries 74, 76 of the control and power source module.

As illustrated in FIG. 2, power is generally delivered unregulated from first or second battery 74, 76 via switch 66 to driver 72 and speaker 70. However, power management module 68 manages power delivered from first or second battery 74, 76 via switch 66 through connector 26 and cable 18 to pump 14. Power management module 68 may include circuitry for properly and safely delivering power to drive the motor of pump 14 including, e.g., power measurement, power regulation, bridging (waveform generation), both thermal and electrical overload detection and protection, and feedback circuitry for receiving signals back from pump 14 and communicating them to processor 60. In some examples, power management module 68 may also include circuitry for sending and receiving communication signals through a transcutaneous energy transfer system (TETS) inductive link.

Figure 3:
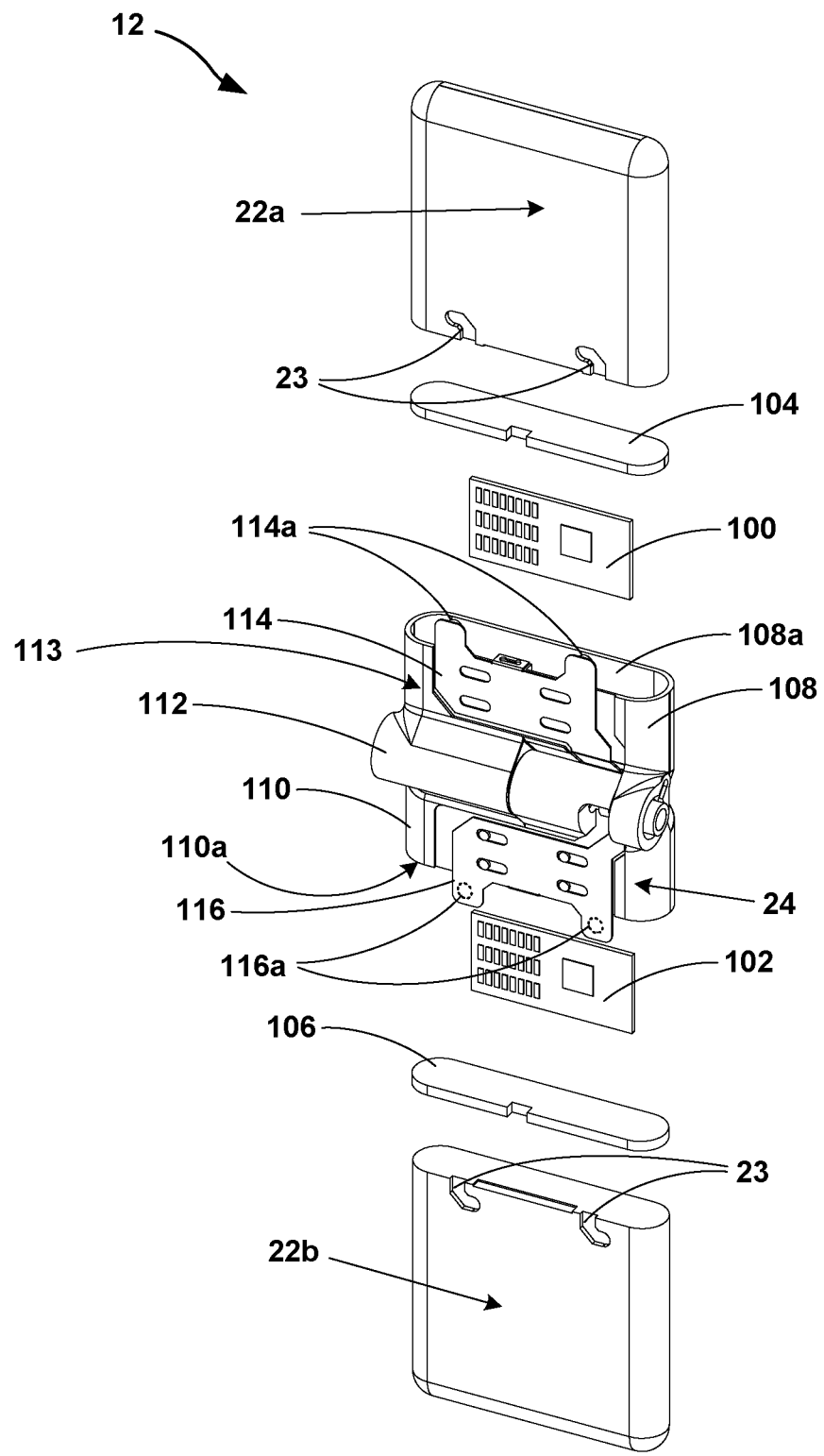
FIG. 3 is an exploded view of an example configuration of the control and power source module of FIG. 1.

FIG. 3 is a partial exploded view of an example configuration of control and power source module 12, which includes first and second battery packs 22*a*, 22*b*, hinged housing 24, first and second control circuit boards 100, 102, and first and second battery connection plates 104, 106. Hinged housing 24 includes first and second halves 108, 110, hinge 112, and battery locking mechanism 113. First and second halves 108, 110 of hinged housing 24 respectively include first and second chambers 108*a*, 110*a*. Battery locking mechanism 113 includes first and second battery lock plates 114, 116. First and second battery packs 22*a*, 22*b* are connected to and protrude from first and second chambers 108*a*, 110*a*, respectively, of hinged housing 24. First and second control circuit boards 100, 102 are arranged within first and second chambers 108*a*, 110*a*, respectively, of hinged housing 24 adjacent to respective ones of first and second battery packs 22*a*, 22*b*. Interposed between and connecting first and second battery packs 22*a*, 22*b* to first and second chambers 108*a*, 110*a*, respectively, of hinged housing 24 and respective first and second control circuit boards are first and second battery connection plates 104, 106.

First and second battery packs 22*a*, 22*b* each include channels 23, which are configured to receive posts 114*a*, 116*a* (see also FIGS. 6A, 7A, and 8B) protruding from battery lock plates 114, 116, respectively. Posts 114*a*, 116*a* and channels 23 are configured to prevent each of first and second battery packs 22*a*, 22*b* from being removed from control and power source module 12 without battery locking mechanism 113 being actuated by, e.g., displacing one of first or second battery locking plates 114, 116 laterally. The operation of battery locking mechanism 113 will be described in detail with reference to FIGS. 5-10.

The configuration of control and power source module 12 including first and second battery packs 22*a*, 22*b* and hinged housing 24, as illustrated in FIG. 3, enables the control and power source module to assume a number of form factors to accommodate a variety of wearable configurations for patient 20. In particular, first and second battery packs 22*a*, 22*b* are connected to hinged housing 24 to form a clam shell assembly configured to fold the first and second battery packs in a generally parallel stacked relationship with one another, as illustrated in FIGS. 4A and 4B, which are front and side elevation views, respectively, of a schematic illustration of control and power source module 12. FIG. 4C is an elevation side view of a schematic illustration of control and power source module 12 with hinged housing 24 rotated about axis of rotation 120 such that first and second battery packs 22*a*, 22*b* are in generally co-planar relationship with one another and are both protruding in opposing directions from first and second chambers 108*a*, 110*a*, respectively, of the hinged housing. In this manner, control and power source module 12 may be worn comfortably by patient 20 in a variety of configurations. For example, module 12 may be worn in a pocket of an article of clothing of patient 20 in either the battery stacked configuration of FIGS. 4A and 4B or the generally parallel configuration of FIG. 4C.

The overall size of control and power source module may be defined by, as illustrated in FIGS. 4A and 4B, a width W, a length L, and a depth D of the device (the depth corresponds to the device with first and second battery packs 22*a*, 22*b* arranged in the generally parallel stacked relationship with one another). In one example, control and power source module 12 may be sized such that the device has a width W in a range from approximately 50 millimeters to approximately 90 millimeters, a length in a range from approximately 80 millimeters to approximately 180 millimeters, and a depth in a range from approximately 12 millimeters to approximately 25 millimeters.

Connector 26 is shown in the view of FIG. 4A, along with cable 18 extending from the connector. Connector 26 is generally configured to receive elongated cable 18 such that the cable extends from the connector at hinged housing 24 along a path that is substantially perpendicular to an axis of rotation 120 of the hinged housing. In some examples, connector 26 is rotatably coupled to hinged housing 24 such that the connector is capable of rotating with respect to the hinged housing. In other examples, connector 26 is coupled to hinged housing 24 such that the connector rotates with one of first battery pack 22*a* or second battery pack 22*b*. Additionally, in some examples, connector 26 may be rotatably coupled to hinged housing 24 such that the connector is capable of rotating in two-dimensions about axis of rotation 120 of the hinged housing, while, in other examples, connector 26 may be rotatably coupled to hinged housing 24 such that the connector is capable of rotating in three-dimensions with respect to the hinged housing.

Figure 5:
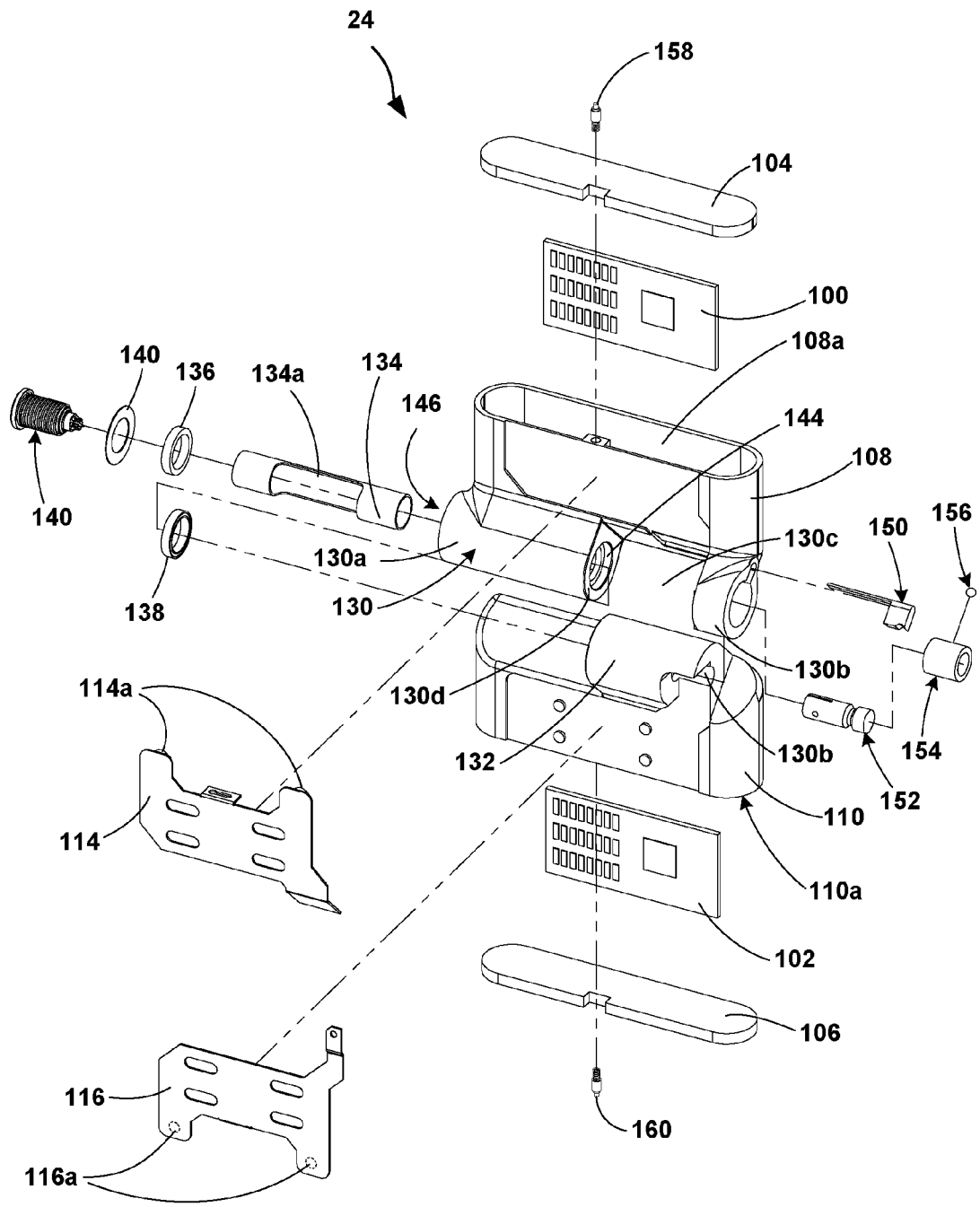
FIG. 5 is an exploded view of an example hinged housing of a control and power source module.

FIG. 5 is an exploded view of an example configuration of hinged housing 24, which includes first and second halves 108, 110, hinge 112, and battery locking mechanism 113. The example of FIG. 5 also includes first and second control circuit boards 100, 102, which are respectively configured to be arranged within first and second chambers 108*a*, 110*a* of first and second halves 108, 110 of hinged housing 24. Hinge 112 includes first and second barrels 130, 132 of hinged housing 24, hinge pin 134, first hinge seal 136, second hinge seal 138, washer 140, and receptacle 142.

In FIG. 5, first and second barrels 130, 132 are connected to respective first and second halves 108, 110 of hinged housing 24. First barrel 130 includes first portion 130*a* and second portion 130*b* offset from the first portion by gap 130*c*. First portion 130*a* may be generally configured for cooperation with hinge pin 134. Second portion 130*b* of first barrel 130 may be configured for cooperation with components of battery locking mechanism 113, as described in greater detail below. Second barrel 132 is configured to be received in gap 130*c* between first and second portions 130*a*, 130*b* of first barrel 130. First portion 130*a* of first barrel 130, and second barrel 132 each include respective bores 130*d*, 132*a*, both of which bores are generally sized to receive hinge pin 134.

In the example of FIG. 5, hinge pin 134 is generally formed as an elongated annular pin within which various components of control and power source module 12 may be arranged including, e.g. control electronics for the device or electrical conduits that may be connected to the control electronics and/or first and/or second battery packs 22*a*, 22*b*. However, in other examples a hinge pin of hinged housing 24 may be formed as a solid elongated post without a hollow central portion. In some examples, hinge pin 134 may be configured to rotate with respect to at least one of first or second halves 108, 110 of hinged housing 24. Hinge pin 134 also includes aperture 134*a* through which, e.g., electrical connectors, e.g. wires, may be passed from first chamber 108*a* of first half 108 of hinged housing 24 to second chamber 110*a* of second half 110 of the hinged housing.

Hinge 112 also includes first and second hinge seals 136, 138, respectively. First hinge seal 136 is configured to surround and seal a portion of the outer surface of hinge pin 130 at an interface between the hinge pin, first barrel 130, and receptacle 142. Second hinge seal 136 is configured to surround and seal a portion of the outer surface of hinge pin 130 at an interface between first barrel 130 and second barrel 132. In the example of FIG. 5, first barrel 130 includes first and second counterbores 144 and 146 configured to receive first and second hinge seals 136, 138, respectively.

Generally speaking, first and second hinge seals 136, 138 are configured to permit relative rotation of first and second halves 108, 110 of hinged housing 24, while substantially inhibiting ingress of material into either of first or second chambers 108a, 110a of the hinged housing. In one example, one or both of first and second hinge seals 136, 138 includes a garter spring seal configured wrap around and seal an outer surface of hinge pin 130. In some examples, one or both of first and second hinge seals 136, 138 includes a garter spring seal including a canted coil spring, which provide a substantially constant load over a range of displacements of the spring to allow greater dimensional variances in mechanical assemblies without variances in spring force.

Example hinged housing 24 of FIG. 5 also includes battery locking mechanism 113, which includes first and second battery lock plates 114, 116, flange 150, pin 152, sleeve 154, ball 156, and first and second ejection pins 158, 160. Flange 150 is connected to first battery lock plate 114 such that displacement of the lock plate, e.g. lateral displacement generally in a direction parallel to axis of rotation 120 of hinged housing 24, causes a corresponding displacement of the flange. Similarly, pin 152 is connected to second battery lock plate 116 such that displacement of the lock plate, e.g. lateral displacement generally in a direction parallel to axis of rotation 120 of hinged housing 24, causes a corresponding displacement of the pin. In particular, flange 116b of second lock plate 116 is configured to be received in slot 152a of pin 152. To secure flange 116b in slot 152a, a second pin may be received in hole 152b of pin 152 such that it passes through hole 116c in flange 116b of second battery lock plate 116. As will be described in greater detail below, first and second ejection pins 158, 160 cooperate with first and second battery lock plates 114, 116, respectively, to eject first and second battery packs 22a, 22b when the lock plates are actuated.

The function of battery locking mechanism 113 is described in detail with reference to FIGS. 6-11. However, generally speaking, locking mechanism 113 is configured to independently lock each of first and second battery packs 22a, 22b to first and second halves 108, 110, respectively, of hinged housing 24. In order to prevent interruption of circulation support of heart 30 of patient 20 by LVAD 10 (see FIG. 1), battery locking mechanism 113 acts to prevent both first and second battery packs 22a, 22b from being disconnected from hinged housing 24 simultaneously. In this manner, first and second batteries 74, 76 of first and second battery packs 22a, 22b (see FIG. 2), respectively, generally function as primary and back-up power sources for pump 14 of LVAD 10 (see FIG. 1) such that power is delivered to the pump without interruption.

FIGS. 6-10 illustrate operation of an example of battery locking mechanism 113 included in hinged housing 24 of control and power source module 12. It is noted that in order to simplify the illustrations of FIGS. 6-10, first and second battery packs 22a, 22b are not shown connected to hinged housing 24. FIGS. 6A and 6B are perspective and detail views of first battery lock plate 114, which is configured to connect to battery pack 22a, in a locked position in which first the battery pack cannot be removed from hinged housing 24. FIGS. 7A and 7B are perspective and detail views of second battery lock plate 116, which is configured to connect to second battery pack 22b, in a locked position in which the second battery pack cannot be removed from hinged housing 24. FIGS. 8A-8C detail the positions of flange 150, pin 152, sleeve 154, and ball 156 when both first and second battery lock plates 114, 116 are in a locked position. FIGS. 9A-9C illustrate actuation of first battery lock plate 114 to release first battery pack 22a and lock second battery lock plate 116 against actuation to prevent second battery pack 22b from simultaneously being removed. FIGS. 10A-10C illustrate actuation of second battery lock plate 116 to release second battery pack 22b and lock first battery lock plate 114 against actuation to prevent first battery pack 22a from simultaneously being removed.

FIGS. 6A-8C illustrate battery locking mechanism 113 in a position with both first and second battery packs 22a, 22b connected to hinged housing 24. In this position of battery locking mechanism 113, either first battery pack 22a or second battery pack 22b may be removed from hinged housing by actuating either first battery lock plate 114 or second battery lock plate 116, respectively. FIGS. 6A and 6B illustrate first battery lock plate 114 in a locked position, and, in particular, illustrate detail of first ejection pin 158 in a retracted state in which first battery pack 22a is not ejected from hinged housing and the first lock plate may be actuated by sliding the plate laterally. In FIGS. 6A and 6B, first ejection pin 158 engages slot 170 in flange 172 of first battery lock plate 114. In the position of FIGS. 6A and 6B, ejection pin 158 engages slot 170 such that first battery lock plate 114 may be displaced laterally.

FIGS. 7A and 7B illustrate second battery lock plate 116 in a locked position, and, in particular, illustrate detail of second ejection pin 160 in a retracted state in which second battery pack 22b is not ejected from hinged housing 24 and the first lock plate may be actuated by sliding the plate laterally. In FIGS. 7A and 7B, second ejection pin 160 engages slot 174 in flange 176 of second battery lock plate 116. In the position of FIGS. 7A and 7B, second ejection pin 160 engages slot 174 such that second battery lock plate 116 may be displaced laterally.

In some examples, one or both of first and second battery lock plates 114, 116 are biased into the locked position shown in FIGS. 6A-7B. For example, first and second battery lock plates 114, 116 may be spring loaded such that actuation to displace the plates laterally and thereby release first and second battery packs 22a, 22b requires overcoming and compressing a spring that biases the plates into the locked position.

Figure 8A:
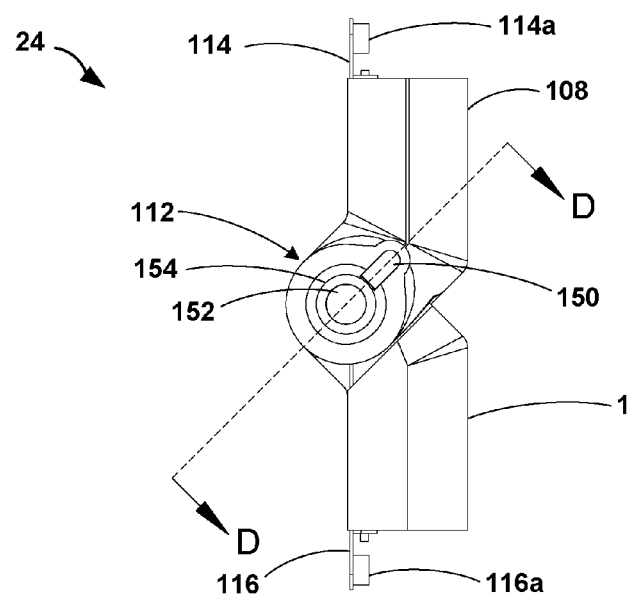
FIGS. 8A-8C are elevation and section views that detail the positions of a number of components of an example battery locking mechanism in a locked position.
Figure 8C:
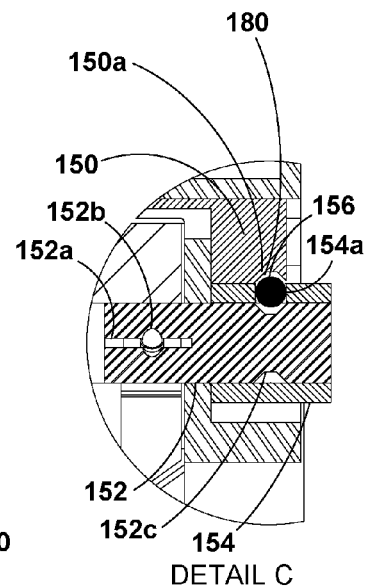
Figure 8B:
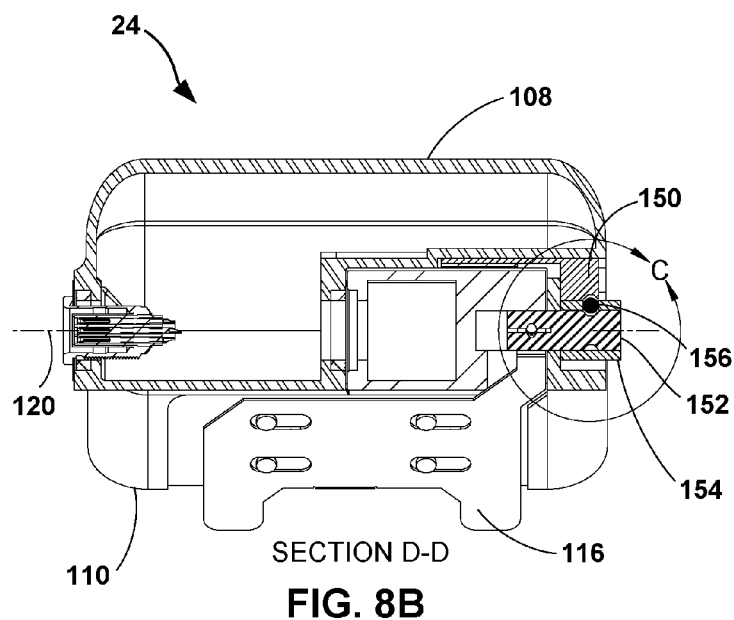

FIGS. 8A-8C the positions of flange 150, pin 152, sleeve 154, and ball 156 when both first and second battery lock plates 114, 116 are in a locked position, as shown in FIGS. 6A-7B. FIG. 8A is an elevation side view of hinged housing 24. FIG. 8B is a section view of hinged housing 24 cut along section line D-D of FIG. 8A. FIG. 8C is a detail view of components of locking mechanism 113 incorporated into hinge 112 of hinged housing 24. In FIGS. 8A-8C, battery locking mechanism 113 includes first and second battery lock plates 114, 116, flange 150, pin 152, sleeve 154, ball 156, and first and second ejection pins 158, 160. Flange 150 is connected to first battery lock plate 114 such that displacement of the lock plate, e.g. lateral displacement generally in a direction parallel to axis of rotation 120 of hinged housing 24, causes a corresponding displacement of the flange. Similarly, pin 152 is connected to second battery lock plate 116 such that displacement of the lock plate, e.g. lateral displacement generally in a direction parallel to axis of rotation 120 of hinged housing 24, causes a corresponding displacement of the ping. In particular, flange 116a of second lock plate 116 is configured to be received in slot 152a of pin 152. To secure flange 116a in slot 152a, a second pin may be received in hole 152b of pin 152 such that it passes through hole 116b in flange 116a of second battery lock plate 116.

Flange 150 includes channel 150a. Pin 152 includes channel 152c. Finally, sleeve 154 includes slot 154a. Channels 150a and 152c and sleeve 154a form cavity 180 within which ball 156 is arranged. In the position of FIGS. 6A-8C, cavity 180 formed by channels 150a and 152c and sleeve 154a is large enough to allow some clearance for movement of ball 156 within the cavity.

FIGS. 9A-9C illustrate actuation of first battery lock plate 114 to release first battery pack 22a and lock second battery lock plate 116 against actuation to prevent second battery pack 22b from simultaneously being removed. FIGS. 9A and 9B are perspective and detail views, respectively, of hinged housing 24 with first battery lock plate 114 actuated to release first battery pack 22a. FIG. 9C is a partial section view cut along section line D-D of FIG. 8A showing the details of the components of battery locking mechanism 113 incorporated into hinge 112 of hinged housing 24. In FIGS. 9A-9C, first battery lock plate 114 is actuated by displacing the lock plate laterally. First ejection pin 158 slides along slot 170 in flange 172 of first battery lock plate 114 until the spring loaded pin is released to push on first battery pack 22a and lock the first battery lock plate into the actuated position. In the released position of first ejection pin 158 shown in detail in FIG. 9B, first battery lock plate 114 cannot displace laterally until the ejection pin is pushed down to permit it to slide within slot 170.

Displacing first battery lock plate 114 laterally causes flange 150, which is connected to the first lock plate, to displace as shown in FIG. 9C. As flange 150 is displaced, ball 156 is pushed down into slot 154a of sleeve 154 and channel 152c of pin 152. The displacement of flange 150 and ball 156 effective reduces the size of cavity 180 within which ball 156 is arranged such that ball 156 locks pin 152 into place. Locking pin 152 into place also causes second battery lock plate 116, which is connected to the pin via flange 116b in slot 152a, to be locked into place. Locking second battery lock plate 116 into place prevents second battery pack 22b from being disconnected from hinged housing 24 simultaneously with first battery pack 22a.

FIGS. 10A-10C illustrate actuation of second battery lock plate 116 to release second battery pack 22b and lock first battery lock plate 114 against actuation to prevent first battery pack 22a from simultaneously being removed. FIGS. 10A and 10B are perspective and detail views, respectively, of hinged housing 24 with second battery lock plate 116 actuated to release second battery pack 22b. FIG. 9C is a partial section view cut along section line D-D of FIG. 8A showing the details of the components of battery locking mechanism 113 incorporated into hinge 112 of hinged housing 24. In FIGS. 10A-10C, second battery lock plate 116 is actuated by displacing the lock plate laterally. Second ejection pin 160 slides along slot 174 in flange 176 of second battery lock plate 116 until the spring loaded pin is released to push on second battery pack 22b and lock the second battery lock plate into the actuated position. In the released position of second ejection pin 160 shown in detail in FIG. 10B, second battery lock plate 116 cannot displace laterally until the ejection pin is pushed down to permit it to slide within slot 174.

Displacing second battery lock plate 116 laterally causes pin 152, which is connected to the second lock plate, to displace as shown in FIG. 10C. As pin 152 is displaced, ball 156 is pushed up into slot 154a of sleeve 154 and channel 150a of flange 150. The displacement of pin 152 and ball 156 effective reduces the size of cavity 180 within which ball 156 is arranged such that ball 156 locks flange 150 into place. Locking flange 150 into place also causes first battery lock plate 114, which is connected to the flange, to be locked into place. Locking first battery lock plate 114 into place prevents first battery pack 22a from being disconnected from hinged housing 24 simultaneously with pin 152 battery pack 22b.

Locking mechanism 113 illustrated in FIGS. 6-10 is configured to independently lock each of first and second battery packs 22a, 22b to first and second halves 108, 110, respectively, of hinged housing 24. In order to prevent interruption of circulation support of heart 30 of patient 20 by LVAD 10 (see FIG. 1), battery locking mechanism 113 acts to prevent both first and second battery packs 22a, 22b from being disconnected from hinged housing 24 simultaneously. In this manner, first and second batteries 74, 76 of first and second battery packs 22a, 22b (see FIG. 2), respectively, generally function as primary and back-up power sources for pump 14 of LVAD 10 (see FIG. 1) such that power is delivered to the pump without interruption. Additionally, by incorporating the locking feature of locking mechanism 113 including flange 150, pin 152, sleeve 154, and ball 156 into hinge 112 of hinged housing 24, the battery locking mechanism may function independent of the rotational position of first and second halves 108, 110 of the hinged housing.

Figure 11:
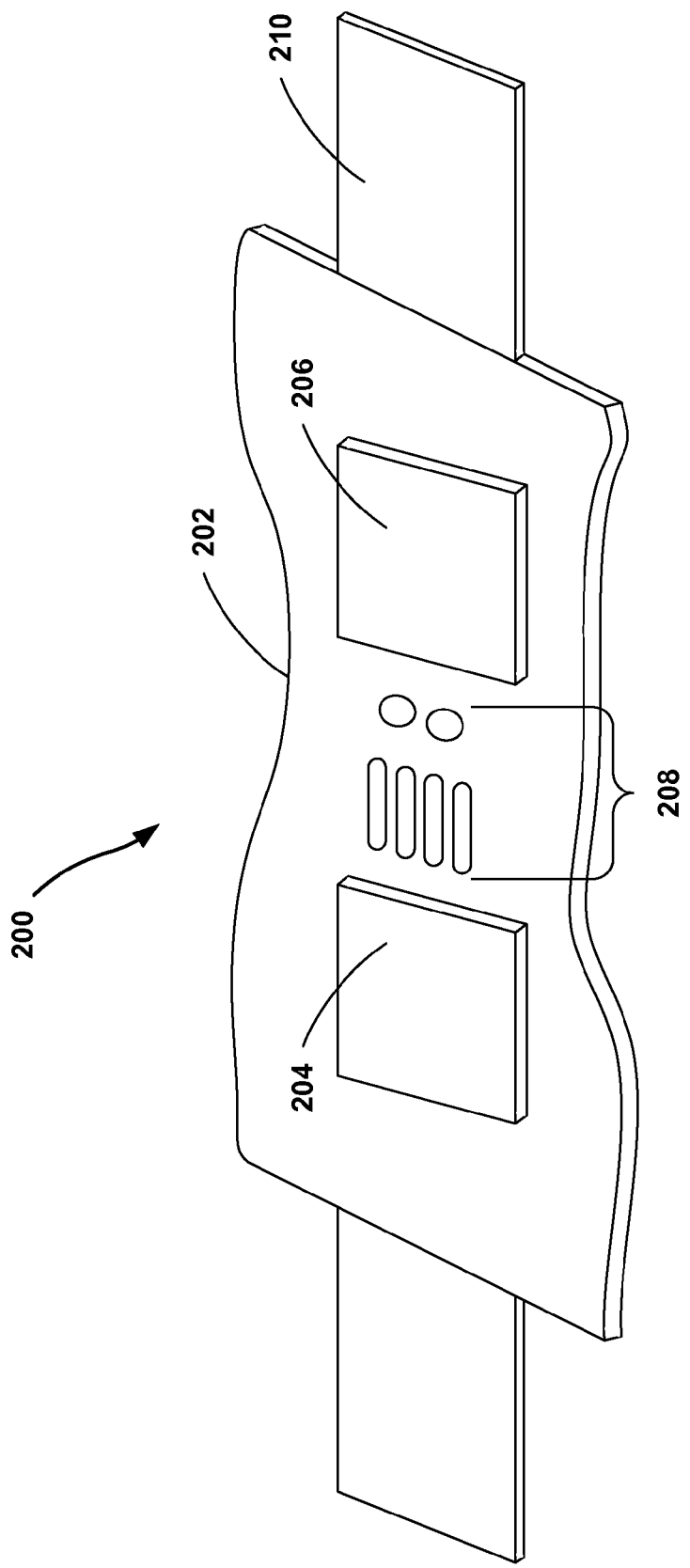
FIG. 11 is a conceptual diagram illustrating an example portable external control and power source module including a malleable housing.

FIG. 11 is a schematic illustration of portable control and power source module 200 that is configured to be worn by a patient, e.g. as a belt. Control and power source module 200 is a portable external device including malleable housing 202 that is configured to be worn by a patient. Control and power source module 200 also includes two batteries 204, 206, status indicators 208, and belt 210. Batteries 204, 206 are connected to malleable housing 202 via, e.g., pockets formed in the housing. A cable may interface with control and power source module 200 to communicate power and other signals between the external module and an implanted pump of a VAD, e.g. pump 14 of LVAD 10 of FIG. 1. Control and power source module 200 also includes control electronics (not shown in FIG. 11) configured to control operation of various components of a VAD including a pump, batteries 204, 206, and status indicators 208. Status indicators 208, generally speaking, are visual indicators incorporated into control and power source module 200 to provide information to a patient including, e.g., a gauge of the remaining charge left in each of batteries 204, 206. Malleable housing 202 of control and power source module 200 permits the module to be comfortably worn by a patient, e.g., by wrapping belt 210 around the patient's waist. In another example, control and power source module 200 may be worn by a patient by wrapping belt 210 around one of the patient's legs or arms.

Malleable housing 202 may be fabricated from a number of materials, including, e.g., various natural and synthetic fabrics, as well as those materials sometimes referred to as smart materials. Generally speaking, smart materials are materials that have properties that can be controlled by external stimuli including, e.g., stress, temperature, moisture, pH, or electric or magnetic fields. Example smart materials from which housing 202 may be fabricated include shape memory alloys like Nitinol, which may be configured to react to the temperature of the body of patient 20 after the patient puts on control and power source module 200 by, e.g., wrapping belt 210 around a leg or arm.

FIG. 12A is a functional block diagram illustrating components of an example external control and power source module 300, which includes removable external battery 302 and internal non-removable back-up battery 304. In a manner similar to example control and power source module 12 of FIG. 2, external battery 302 may be incorporated into battery pack 306, which also includes status indicators 308. Control and power source module 300 also includes connector 310 connected to cable 312. Cable 312 may be connected percutaneously to an implanted pump of a VAD in a manner similar to cable 18 of the example of FIG. 1. Control and power source module 300 includes a variety of electronics, e.g. processor 314, memory 316, telemetry module 318, multiplexer with switch 320, power management module 322, and charger 324. In some examples, control and power source module 12 also includes speaker 324 driven by driver 326 for emitting audible messages to a patient or a caregiver, such as a clinician. The electronics of control and power source module 300 may function in a manner similar to the electronics of control and power source module 12 described with reference to FIG. 2. However, control and power source module 300 provides uninterrupted power to components of a VAD, not by mechanically preventing first and second external batteries from being removed simultaneously, but, instead, by employing one external removable battery 302 as a primary power source and internal non-removable battery 304 as a back-up to bridge operation of the VAD components during recharge of removable battery 302. Internal battery 304 is non-removably connected to control and power source module 300 in the sense that it is not configured to be removed and replaced by users during normal operation of the device. Battery 304 may, of course, be removed from control and power source module 300, e.g. by disassembling the device and disconnecting internal battery 304 from the internal circuitry of the device.

Generally speaking, control and power source module 300 employs two power sources for redundancy and continuous operation. The primary power source is external battery 302, which may be removed to recharge the battery. Although control and power source module 300 is described as including battery 302 as the primary removable power source, in other examples, the module may include an adapter for a DC or AC source. Additionally, in some examples, control and power source module 300 may include an adapter for a DC or AC external power source as a third source of power for the device. The third power source may be used, in some examples, over both external battery 302 and internal battery 304. In the example of FIG. 12A, however, the back-up power source employed in control and power source module 300 is internal battery 304, which may not be removed from the module. When employed for use with a VAD, power will be delivered to the pump of the VAD primarily from external battery 302. If battery 302 becomes depleted and requires removal and recharging, or, if external battery 302 fails, processor 314 of control and power source module 300 automatically toggles to internal battery 304 via switch 320. While external battery 302 is being used, back-up internal battery 304 may be periodically tested by processor 314 to determine a level of charge left in the internal battery. In the event internal battery 304 becomes depleted, processor 314 may control external battery 302 (or any connected external power source) to replenish the internal battery using charger 324. In examples including a third external power source, e.g. a DC or AC external power source, the third power source may be used to charge external battery 302 when it is connected to control and power source module 300. An ideal diode OR may be employed in control and power source module 300 to multiplex the power sources together, e.g. external battery 302 and internal battery 304, while minimizing power consumption in the power union.

In some examples, external battery 302 and back-up internal battery 304 may be configured to have the same or different operational life times. In one example, external battery 302 is configured to operate without recharge for a period of time in a range from approximately 4 hours to approximately 8 hours. In another example, external battery 302 is configured to operate without recharge for a period of time approximately equal to 6 hours. In one example, internal battery 304 is configured to operate without recharge for a period of time in a range from approximately 30 minutes to approximately 2 hours. In one example, internal battery 304 is configured to operate without recharge for a period of time approximately equal to 1 hour. Employing a smaller non-removable battery 304 in control and power source module 300 may act to reduce the complexity and cost of the device by removing the necessity for two full-size external batteries and a mechanical battery locking mechanism.

As noted above, in some examples, control and power source module 300 may include an adapter for an external power source as a third source of power for the device. In examples in which a third source is employed for power for control and power source module 300, the device may also employ flexible on-board charging techniques to provide users the ability to charge external battery 302 and/or internal battery 304 while connected to the device. The third power source may be either an additional external battery or another external power source, e.g. a DC or AC external power source. A series of field-effect transistors (FETs) or other switches may allow one or more algorithms, e.g. stored on memory 316 and executed by processor 314 of control and power source module 300 to control which of external battery 302 or internal battery 304 is being charged and hardware may select either external battery 302 or preferably the third power source to be employed for charging the other power sources of the device. Additionally, the same or different algorithms executed by processor 314 to control which source is charged may also control the battery charge profile based on the state of the external battery 302 and internal battery 304 and the third power source.

FIG. 12B is an example circuit diagram that may be employed in control and power source module 300 to provide flexible on-board charging. In FIG. 12B, three power sources external battery 302, internal battery 304, and third external AC source 328 are connected to a charger circuit. A diode-OR is performed on the two power inputs to the charger V_EBATT and V_AC, which may correspond to, e.g. external battery 302 and third external AC source 328. The charger sends the output VCHGOUT to the FETs for routing to the batteries of control and power source module 300 that are being charged. The FETs may be controlled by processor 314.

FIG. 12C is an example of control and power source module 300 in non-hinged housing 330. In FIG. 12C, external battery 302 and internal non-removable back-up battery 304 (shown in hidden line) of control and power source module 300 are arranged within non-hinged housing 330. However, external battery 302 is removably connected to control and power source module 300 such that the external battery may be removed via, e.g., a bay on one side of housing (not shown) that may be accessed by a user via a removable cover (not shown). In a manner similar to the hinged design illustrated in and described with reference to the example of FIGS. 1-10C, hinged housing 330 of control and power source module 300 may be sized such that the housing has a width in a range from approximately 50 millimeters to approximately 90 millimeters, a length in a range from approximately 80 millimeters to approximately 180 millimeters, and a depth in a range from approximately 12 millimeters to approximately 25 millimeters.

In some examples, external control and power source modules according to this disclosure may be employed as transcutaneous energy transfer systems (TETS), in lieu of powering and controlling an implanted pump of a VAD. FIG. 13 is a schematic illustration of VAD 400 including control and power source module 402 that functions as a TETS. VAD 400 includes control and power source module 402, connector 404, TETS cable 405 including TETS primary coil 406, TETS secondary coil 408, and pump 410. In FIG. 13, TETS cable 405 including TETS primary coil 406 is separate from and connected to control and power source module via connector 404. However, in other examples, TETS primary coil 406 may be incorporated into control and power source module 402. Control and power source module 402 is connected to implanted pump 410 via percutaneous cable 412, which may pass through an incision in the body of a patient. Also implanted in the patient is TETS secondary coil 408. Although VAD 400 is illustrated in FIG. 13 with TETS secondary coil 408 as a separate component from pump 410, in other examples, the TETS secondary coil may be incorporated into pump 410.

Control and power source module 402 may, in some examples, employ a 3-phase bridge to control an electric motor that drives implanted pump 410. Two or three of these half bridges employed in module 402 may deliver power to TETS primary coil 406 contained in TETS cable 405. In some examples of control and power source module 402, the 3-phase bridge may also be configured to sense current amplitude and phase of the motor of pump 410. Placing TETS cable 405 and thereby primary coil 406 on the surface of the skin of the patient will inductively couple the primary coil to TETS internal secondary coil 408 below the skin. Power transmitted from primary coil 406 to secondary coil 408 may be conditioned with circuitry included in the secondary coil, pump 410, or another device. A control feedback loop utilizing either a RF link or the inductive coupling between TETS primary coil 406 and secondary coil 408 may be employed to regulate the circuitry in the primary coil by, e g taking advantage of the relationship between the current of the primary coil and the voltage of the secondary coil.

VADs in accordance with examples described in this disclosure may, in addition to the foregoing features, employ wireless energy transfer components and techniques. There may be several implementations of wireless energy transfer in a VAD system including, e.g., transferring energy from a charging pad to a battery, a battery to external VAD controller, and a battery to a VAD controller implanted within a patient's body. Generally speaking, however, wireless energy transfer in VADs according to this disclosure may be accomplished by employing a driver and/or tank circuit in the primary, i.e. energy source, a tank circuit and rectifier in the secondary, i.e. energy sink, and a control feedback signal from the secondary to the primary via either an inductive coupling or a RF link. Such wireless energy transfer techniques may provide benefits including improved user convenience, elimination of a major source of infection, waterproofing and reliability.

The foregoing examples disclose a number of concepts related to control and power sourced modules employed in VADs. Although the disclosed examples have, in some cases, been described in the context of particular physical and/or logical implementations of a control and power source module or other VAD component, combinations other than those specifically described are possible. For example, the hinged housing design illustrated in and described with reference to the two external battery control and power source module of FIGS. 1-10C may be implemented in a one external and one internal battery control and power source module, as in the examples of FIGS. 12A and 12B. Similarly, the non-hinged housing design of FIG. 12C, although described with reference to the external and internal battery design of FIGS. 12A and 12B, may be implemented with a two external battery control and power source module, as illustrated in and described with reference to the examples of FIGS. 1-10C.

Techniques described in this disclosure related to functions executed by control electronics of a VAD device may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Some techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, magnetic media, optical media, or other computer readable media.

Various examples have been described. These and other examples are within the scope of the following claims.

The invention claimed is:

1. A portable external device for a mechanical circulation support (MCS) system comprising:
   a first power source;
   a second power source, wherein at least one of the first power source and the second power source is configured to power an implantable pump of the MCS system;
   a hinged housing interposed between and configured to receive the first and second power sources; and
   control electronics arranged within the hinged housing and configured to control the implantable pump.

2. The device of claim 1 further comprising a connector electrically connected to the control electronics and coupled to the hinged housing.

3. The device of claim 2, wherein the connector is configured to receive at least one elongated electrical cable such that the cable extends from the connector at the hinged housing along a path that is substantially perpendicular to an axis of rotation of the hinged housing.

4. The device of claim 2, wherein the connector is rotatably coupled to the hinged housing such that the connector is capable of rotating with respect to the hinged housing.

5. The device of claim 2, wherein the connector is coupled to the hinged housing such that the connector rotates with one of the first power source or the second power source.

6. The device of claim 1, wherein the control electronics are arranged within the hinged housing proximate to one of the first power source or the second power source.

7. The device of claim 1, wherein the control electronics are arranged within a hinge of the hinged housing approximately equidistant from the first and second power sources.

8. The device of claim 1, wherein the hinged housing comprises:
   a first half configured to receive one of the first power source or the second power source;
   a second half configured to receive the other of the first power source or the second power source; and
   a hinge pin received by the first half and the second half.

9. The device of claim 8, wherein the hinge pin comprises an elongated annular pin within which at least one of at least a portion of the control electronics or at least one electrical conduit connected to at least one of the control electronics, the first power source, or the second power source is received.

10. The device of claim 8, wherein the hinge pin is configured to rotate with respect to at least one of the first half or the second half.

11. The device of claim 1 further comprising a telemetry module configured to wirelessly communicate with a display device arranged distal to the portable external device.

12. The device of claim 11, wherein the telemetry module is configured for radio frequency communications with a display device.

13. The device of claim 12, wherein the telemetry module is configured to wirelessly communicate with a display device via RF according to at least one of an 802.11, Bluetooth, Bluetooth Low Energy, MICS, or IRDA specification set.

14. The device of claim 1, wherein the hinged housing comprises at least one hinge seal configured to permit relative rotation of the first and second power sources and substantially inhibit ingress of material into the hinged housing.

15. The device of claim 14, wherein the hinge seal comprises a garter spring seal.

16. The device of claim 15, wherein the garter spring seal comprises a canted coil spring.

17. The device of claim 15, wherein the hinged housing comprises:
   a first half configured to receive one of the first power source or the second power source;
   a second half configured to receive the other of the first power source or the second power source; and
   a hinge pin received by the first half and the second half, wherein the garter spring seal surrounds an outer surface of the hinge pin at an interface between the hinge pin and the first and second halves.

18. The device of claim 1, wherein the hinged housing comprises a locking mechanism configured to independently lock each of the first and the second power sources to the hinged housing.

19. The device of claim 18, wherein the locking mechanism prevents both the first and the second power sources from being disconnected from the hinged housing simultaneously.

20. The device of claim 1, wherein at least one of the first and second power sources comprises a battery.

21. The device of claim 1, wherein the first power source comprises a first battery and the second power source comprises a second battery.

22. The device of claim 21, wherein the first and second batteries are connected to the hinged housing to form a clam shell assembly configured to fold the first and second batteries in a generally parallel stacked relationship with one another and rotate the first and second batteries from the stacked relationship into generally co-planar relationship with one another with each of the first and second batteries extending in opposing directions from the hinged housing.

23. The device of claim 22, wherein at least one of the first or the second battery comprises a lithium-ion (Li-ion), lithium polymer (Lipoly), nickel-metal hydride (NiMH), or nickel-cadmium (NiCd) battery.

24. The device of claim 22, wherein the first and second batteries are arranged in the generally parallel stacked relationship such that the portable external device comprises a width in a range from approximately 50 millimeters to approximately 90 millimeters, a length in a range from approximately 80 millimeters to approximately 180 millimeters, and a depth in a range from approximately 12 millimeters to approximately 25 millimeters.

25. A mechanical circulation support system comprising:
   an implantable pump; and
   a portable external device comprising:
      a first power source;
      a second power source;
      a hinged housing interposed between and configured to receive the first and second power sources; and
      control electronics arranged within the hinged housing, wherein at least one of the first power source and the second power source is configured to power the implantable pump.

26. The system of claim 25 further comprising a connector electrically connected to the control electronics and coupled to the hinged housing.

27. The system of claim 26, wherein the connector is configured to receive at least one elongated electrical cable such that the cable extends from the connector at the hinged housing along a path that is substantially perpendicular to an axis of rotation of the hinged housing.

28. The system of claim 26, wherein the connector is rotatably coupled to the hinged housing such that the connector is capable of rotating with respect to the hinged housing.

29. The system of claim 28, wherein the connector is capable of rotating in two-dimensions about an axis of rotation of the hinged housing.

30. The system of claim 28, wherein the connector is capable of rotating in three-dimensions with respect to the hinged housing.

31. The system of claim 26, wherein the connector is coupled to the hinged housing such that the connector rotates with one of the first power source or the second power source.

32. The system of claim 25, wherein the control electronics are arranged within the hinged housing proximate to one of the first power source or the second power source.

33. The system of claim 25, wherein the control electronics are arranged within a hinge of the hinged housing approximately equidistant from the first and second power sources.

34. The system of claim 25, wherein the hinged housing comprises:
a first half configured to receive one of the first power source or the second power source;
a second half configured to receive the other of the first power source or the second power source; and
a hinge pin received by the first half and the second half.

35. The system of claim 34, wherein the hinge pin comprises an elongated annular pin within which at least one of at least a portion of the control electronics or at least one electrical conduit connected to at least one of the control electronics, the first power source, or the second power source is received.

36. The system of claim 34, wherein the hinge pin is configured to rotate with respect to at least one of the first half or the second half.

37. The system of claim 34 further comprising a telemetry module configured to wirelessly communicate with a display device arranged distal to the portable external device.

38. The system of claim 37, wherein the telemetry module is configured for radio frequency communications with a display device.

39. The system of claim 38, wherein the telemetry module is configured to wirelessly communicate with a display device via RF according to at least one of an 802.11, Bluetooth, Bluetooth Low Energy, MICS, or IRDA specification set.

40. The system of claim 25, wherein the hinged housing comprises at least one hinge seal configured to permit relative rotation of the first and second power sources and substantially inhibit ingress of material into the hinged housing.

41. The system of claim 40, wherein the hinge seal comprises a garter spring seal.

42. The system of claim 41, wherein the garter spring seal comprises a canted coil spring.

43. The system of claim 41, wherein the hinged housing comprises:
a first half configured to receive one of the first power source or the second power source;
a second half configured to receive the other of the first power source or the second power source; and
a hinge pin received by the first half and the second half, wherein the garter spring seal surrounds an outer surface of the hinge pin at an interface between the hinge pin and the first and second halves.

44. The system of claim 25, wherein the hinged housing comprises a locking mechanism configured to independently lock each of the first and the second power sources to the hinged housing.

45. The system of claim 44, wherein the locking mechanism prevents both the first and the second power sources from being disconnected from the hinged housing simultaneously.

46. The system of claim 25, wherein at least one of the first and second power sources comprises a battery.

47. The system of claim 25, wherein the first power source comprises a first battery and the second power source comprises a second battery.

48. The system of claim 47, wherein the first and second batteries are connected to the hinged housing to form a clam shell assembly configured to fold the first and second batteries in a generally parallel stacked relationship with one another and rotate the first and second batteries from the stacked relationship into generally co-planar relationship with one another with each of the first and second batteries extending in opposing directions from the hinged housing.

49. The system of claim 48, wherein at least one of the first or the second battery comprises a lithium-ion (Li-ion), lithium polymer (Lipoly), nickel-metal hydride (NiMH), or nickel-cadmium (NiCd) battery.

50. The system of claim 48, wherein the first and second batteries are arranged in the generally parallel stacked relationship such that the portable external device comprises a width in a range from approximately 50 millimeters to approximately 90 millimeters, a length in a range from approximately 80 millimeters to approximately 180 millimeters, and a depth in a range from approximately 12 millimeters to approximately 25 millimeters.

* * * * *